United States Patent
Pillay et al.

(10) Patent No.: US 9,439,863 B2
(45) Date of Patent: Sep. 13, 2016

(54) PHARMACEUTICAL DOSAGE FORM

(71) Applicant: University of the Witwatersrand, Johannesburg, Johannesburg (ZA)

(72) Inventors: Viness Pillay, Johannesburg (ZA); Yahya Essop Choonara, Johannesburg (ZA); Felix Mashingaidse, Johannesburg (ZA); Pradeep Kumar, Johannesburg (ZA)

(73) Assignee: University of the Witwatersrand, Johannesburg, Johannesburg (ZA)

( * ) Notice: Subject to any disclaimer, the term of this patent is extended or adjusted under 35 U.S.C. 154(b) by 0 days.

(21) Appl. No.: 14/376,907

(22) PCT Filed: Feb. 8, 2013

(86) PCT No.: PCT/IB2013/051052
§ 371 (c)(1),
(2) Date: Aug. 6, 2014

(87) PCT Pub. No.: WO2013/118092
PCT Pub. Date: Aug. 15, 2013

(65) Prior Publication Data
US 2015/0004225 A1  Jan. 1, 2015

(30) Foreign Application Priority Data
Feb. 8, 2012  (ZA) .................. 2011/06578

(51) Int. Cl.
| | |
|---|---|
| *A61K 9/16* | (2006.01) |
| *A61K 31/7072* | (2006.01) |
| *A61K 9/50* | (2006.01) |
| *A61K 9/00* | (2006.01) |
| *A61K 9/20* | (2006.01) |

(52) U.S. Cl.
CPC ........... *A61K 9/1652* (2013.01); *A61K 9/0034* (2013.01); *A61K 9/1647* (2013.01); *A61K 9/1658* (2013.01); *A61K 9/2077* (2013.01); *A61K 9/5031* (2013.01); *A61K 31/7072* (2013.01)

(58) Field of Classification Search
CPC ............. A61K 9/0034; A61K 9/1674; A61K 9/5031; A61K 9/1652; A61K 9/1658; A61K 31/7072; A61K 9/2077
See application file for complete search history.

(56) References Cited

U.S. PATENT DOCUMENTS

| | | | | |
|---|---|---|---|---|
| 5,047,244 A | * | 9/1991 | Sanvordeker | ........... A61F 13/02 424/434 |
| 2006/0127459 A1 | * | 6/2006 | Huang | ................ A61K 9/0034 424/443 |
| 2011/0280922 A1 | * | 11/2011 | Ron | ....................... A61F 13/20 424/431 |

OTHER PUBLICATIONS

Cespi et al., Evaluation of Polymer Mucoadhesiveness by the Use of Acoustic Spectroscopy, AAPS PharSciTech, 2010, 11 (3), 1232-1236.*
Ofokansi et al. Tropical Journal of Pharmaceutical Research, 2007, 6 (4), 825-832.*
Kumar et al.. "Development of pectin based hydrogel membranes for biomedical applications", Int J Plast Technol, Dec. 2010, pp. 213-223, vol. 14, No. 2.
Owen et al., "A Vaginal Fluid Simulant", Contraception, 1999, pp. 91-95, vol. 59.
Pliszczak et al., "Improvement of an encapsulation process for the preparation of pro- and prebiotics-loaded bioadhesive microparticles by using experimental design", European Journal of Pharmaceutical Sciences, 2011, pp. 83-92, vol. 44.
Pliszczak et al., "Mucoadhesion evaluation of polysaccharide gels for vaginal application by using rheological and indentation measurements", Colloids and Surfaces B, Biointerfaces, 2012, pp. 168-174, vol. 92.
Sriamornsak et al., "Study on the mucoadhesion mechanism of pectin by atomic force microscopy and mucin-particle method", Carbohydrate Polymers, 2010, pp. 54-59, vol. 79.
Van Damme et al., "Effectiveness of COL-1492, a nonoxynol-9 vaginal gel, on HIV-1 transmission in female sex workers: a randomised controlled trial", The Lancet, Sep. 28, 2002, pp. 971-977, vol. 360.

* cited by examiner

*Primary Examiner* — Alli Soroush
*Assistant Examiner* — Genevieve S Alley
(74) *Attorney, Agent, or Firm* — The Webb Law Firm

(57) ABSTRACT

This invention relates to pharmaceutical dosage forms, particularly to pH dependent pharmaceutical dosage forms with enhanced and/or prolonged distribution of a pharmaceutical compound at a target site. More specifically, this invention relates to a controlled release intravaginal pharmaceutical dosage form and, more particularly, to a pharmaceutical dosage form which comprises microspheres encapsulated and/or embedded within a bioerodible polymeric matrix, together the microspheres and the matrix are formed into a caplet and/or tablet.

14 Claims, 23 Drawing Sheets

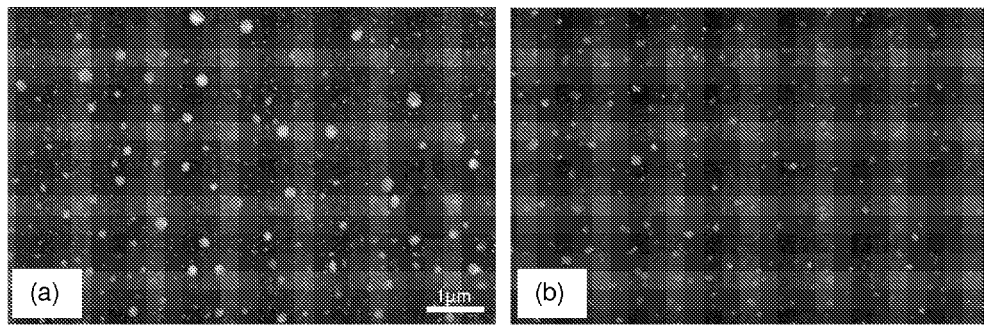
FIGURE 5(A) AND (B):
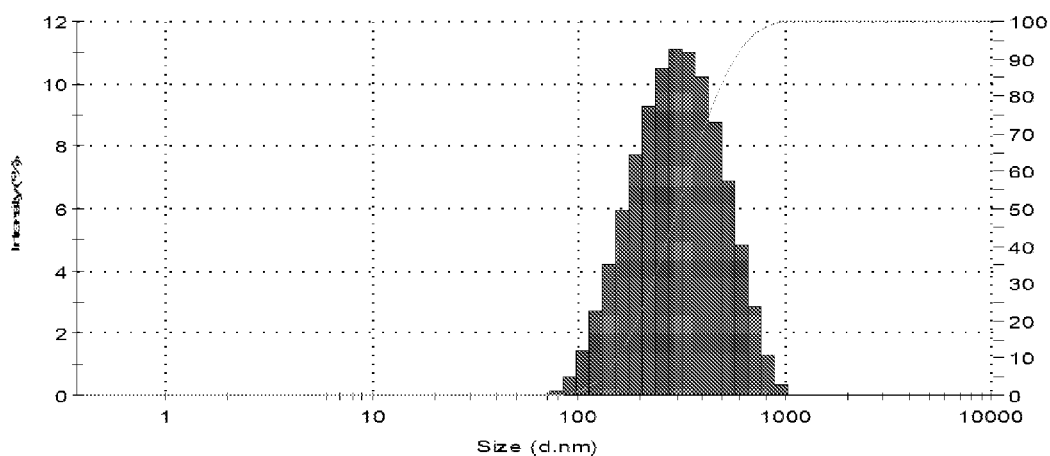
FIGURE 6.
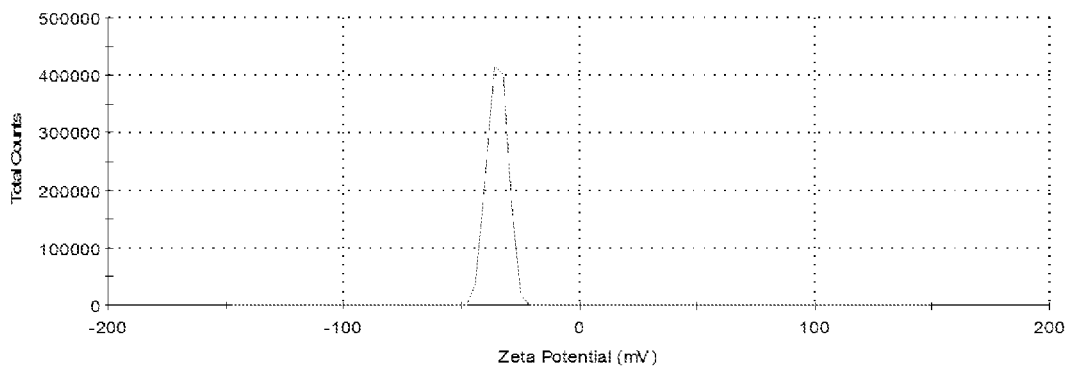
FIGURE 7.

PHARMACEUTICAL DOSAGE FORM

CROSS-REFERENCE TO RELATED APPLICATIONS

This application is the United States national phase of International Application No. PCT/IB2013/051052 filed Feb. 8, 2013, and claims priority to South African Patent Application No. 2011/06578 filed Feb. 8, 2012, the disclosures of which are hereby incorporated in their entirety by reference.

FIELD OF THE INVENTION

This invention relates to pharmaceutical dosage forms, particularly to pH dependent pharmaceutical dosage forms with enhanced and/or prolonged distribution of a pharmaceutical compound at a target site.

In particular this invention relates to a controlled release intravaginal pharmaceutical dosage form and, more particularly, to a pharmaceutical dosage form which comprises microparticles, preferably microspheres encapsulated and/or embedded within a bioerodible polymeric matrix, together the microspheres and the matrix are formed into a caplet and/or tablet. The pharmaceutical dosage form is suitable for delivery of a pharmaceutical compound wherein the microspheres carry the pharmaceutical compound and release said compound in a rate-modulated site-specific manner as the matrix erodes when, in use, the pharmaceutical dosage form is administered intravaginally.

BACKGROUND OF THE INVENTION

The past decade has witnessed a notable increase in research pertaining to microbicides and their associated use in pharmacological applications. One particular area of increased research is HIV/AIDS research.

A substantial amount of research into microbicidal chemical agents that are applied intravaginally to prevent transmission of sexually transmitted diseases, including HIV-1, has been conducted in the recent past. One of the major motives for conducting this research is that these agents can shift the sexually transmitted infection (STI) prevention dominion from male to female.

Many such microbicidal chemical agents have proven to be effective in vitro but this has not been the case in vivo and, in consequence, no anti-HIV-1 microbicide is available on the market. The translational failures of microbicides have been attributed to various factors, among them the fact that some microbicidal agents, though effective in deterring the HIV-1 virus, also diminishes the host's defence mechanisms as exemplified by the nonoxynol-9 gel which disrupts the barrier properties of the vaginal mucosa (Van damme et al., 2002). Other challenges faced in this area of research include the ability to deliver these potent anti-HIV-1 microbicidal agents in a manner in which they retain their potency, tailoring said agents to be successfully distributed in a site specific manner (particularly intravaginally), and controlling their residence time at the specific site such that they are quantitatively sufficient to effectively prevent HIV-1 transmission.

Various pharmaceutical anti-HIV-1 microbicidal formulations have been invented including vaginal tablets, rings, films and gel formulations, most of which are fast, yet short acting delivery systems applied prior to and after coitus. There is a need to develop pharmaceutical dosage forms having an increased residence time at their target sites. There is further a need for a more ergonomic pharmaceutical dosage form to be developed relative to the existing intravaginal pharmaceutical dosage forms on the market, which include gels which have been reported to be messy and sticky. It remains important that the pharmaceutical dosage forms deliver at least one pharmaceutical compound, extensively and exclusively, at a specific target site.

SUMMARY OF THE INVENTION

In accordance with a first aspect of this invention there is provided a pharmaceutical dosage form for releasing, at a target site in the vagina of a human, in a controlled and rate modulated manner, a pharmaceutical compound, said pharmaceutical dosage form comprising:

at least one microparticle, preferably a microsphere, which microsphere comprises a pectin (PEC) framework providing rigidity to the microsphere and porcine gastric mucin (MUC) substantially encapsulated and/or embedded in the pectin (PEC) framework, such that in use, the pharmaceutical dosage form is inserted into the vagina and the pectin (PEC) and porcine gastric mucin (MUC) modulate release of the pharmaceutical compound at the target site in a pH dependent manner, wherein an increase in pH facilitates an increase in the release rate of the pharmaceutical compound from the microsphere and wherein a decrease in pH facilitates a decrease in the release rate of the pharmaceutical compound from the microsphere.

In an example embodiment of the invention the pharmaceutical dosage form comprises a multitude of microspheres.

The pharmaceutical dosage form may release the pharmaceutical compound in a pH dependent manner wherein an alkaline pH facilitates an increase in the release rate of the pharmaceutical compound from the microsphere and wherein an acidic pH facilitates a decrease in the release rate of the pharmaceutical compound from the microsphere.

The microspheres may release the pharmaceutical compound in a pH dependent manner wherein an increase in pH facilitates a conformation change of the porcine gastric mucin (MUC) causing the microsphere's structural integrity to be compromised, in so doing, releasing the pharmaceutical compound.

The microspheres may release the pharmaceutical compound in a pH dependent manner wherein a decrease in pH facilitates maintenance of the structural integrity of the microspheres such that release of the pharmaceutical compound occurs through diffusion-based means. The release occurring because of the microsphere's structural integrity being compromised is greater relative to release through diffusion-based means.

The target site may be the vaginal wall, preferably in the region of the posterior fornix, alternatively the surface of the cervix.

The pharmaceutical dosage form may further comprise polyethylene glycol (PEG), such that when used intravaginally, the polyethylene glycol (PEG) provides a neutral charge hydrophilic coating for the microsphere, the neutral charge hydrophilic coating facilitating passage of the microspheres across vaginal mucus lining the target site, the target site located on the vaginal wall. In an alternative embodiment, the pharmaceutical dosage form may further comprise polyethylene glycol (PEG) such that the formed PEC-MUC-PEG microspheres are monolithic in nature, i.e. the PEC, MUC and PEG are blended to form a microsphere, the PEG component of the PEC-MUC-PEG microsphere having a neutral charge and facilitating passage of the PEC-MUC-PEG microspheres across the vaginal mucus lining the target site.

The polyethylene glycol (PEG) may be low molecular weight polyethylene glycol (PEG), preferably the low molecular weight polyethylene glycol (PEG) having a molecular weight of about 400 g/mol. The porcine gastric mucin (MUC) is preferably porcine gastric mucin type III.

In a particular example embodiment of the invention there is provided for the microspheres to each comprise the pectin (PEC) framework, the porcine gastric mucin (MUC), preferably MUC III, and the low molecular weight polyethylene glycol (PEG), preferably the low molecular weight polyethylene glycol (PEG) having a molecular weight of about 400 g/mol, such that PEC-MUC-PEG microspheres are formed. In use the pectin (PEC) facilitates providing rigidity to the microsphere and modulates intravaginal release of the pharmaceutical compound in a pH dependent manner wherein an increase in pH facilitates an increase in release rate of the pharmaceutical compound and wherein a decrease in pH facilitates a decrease in the release rate of the pharmaceutical compound. The pectin (PEC) framework also acts in use to facilitate interpenetration of the microspheres within vaginal tissue located at the target site, and therefore aids in the distribution of the microspheres around the target site. In use the porcine gastric mucin (MUC) modulates intravaginal release of the pharmaceutical compound in a pH dependent manner wherein an increase in pH facilitates an increase in release rate of the pharmaceutical compound and wherein a decrease in pH facilitates a decrease in the release rate of the pharmaceutical compound. The porcine gastric mucin (MUC) also acts in use to facilitate interpenetration of the microspheres within vaginal tissue located at the target site through interaction with inherent mucin of the vagina located at said target site. Further, in use, the low molecular weight polyethylene glycol (PEG) provides a neutral charge hydrophilic component or coating for the microspheres, the neutral charge hydrophilic component or coating facilitating passage of the microspheres across vaginal mucus lining the target site, the target site located on the vaginal wall. The polyethylene glycol (PEG) further acts in use to facilitate interpenetration of the microspheres within vaginal tissue located at the target site, and therefore aids in the distribution of the microspheres around the target site.

The pharmaceutical dosage form may further comprise a bioerodible polymeric matrix which is associated and/or bonded and/or connected with the microspheres, such that in use, the pharmaceutical dosage form is inserted into the vagina, preferably the posterior fornix, and the bioerodible polymeric matrix erodes over a predetermined time period therein releasing the microspheres which, in turn, release the pharmaceutical compound intravaginally.

The bioerodible matrix may be substantially hydrophobic and the microspheres may be substantially hydrophilic, such that release of pharmaceutical compound via diffusion-based means is inhibited.

The bioerodible polymeric matrix may be selected so as to bioerode at a predetermined rate, therein facilitating the release of the microspheres, the microspheres, in turn, facilitating the release of the pharmaceutical compound to achieve a desired release profile of microspheres and pharmaceutical compound at the target site.

The bioerodible polymeric matrix may comprise an intravaginal microenvironment pH maintenance agent, such that in use, bioerosion of the matrix facilitates the maintenance of an acidic intravaginal pH impeding sexually transmitted infections or diseases and further modulating the release of the pharmaceutical compound from the microspheres.

The bioerodible polymeric matrix may have bioadhesive properties, such that in use, the pharmaceutical dosage form adheres to the vaginal wall, preferably in the region of the posterior fornix, alternatively to the surface of the cervix.

The pharmaceutical dosage form may comprise a binding agent to facilitate binding between the bioerodible polymeric matrix and the microspheres.

There is further provided for the pharmaceutical dosage form to be formed into a caplet, alternatively a tablet, which caplet or tablet comprises the bioerodible polymeric matrix which substantially encapsulates and/or embeds a multitude of microspheres, such that in use, bioerosion of the matrix results in release of the microspheres which, in turn, releases the pharmaceutical compound. The caplet or tablet may be a composite polymeric caplet or tablet.

The bioerodible polymeric matrix may comprise a hydrophilic polymer, alternatively a hydrophobic polymer, further alternatively a blend of hydrophilic and hydrophobic polymers, and for the bioerodible polymeric matrix to comprise at least one polymer selected from the group comprising: poly(acrylic acids) (PAA), poly(lactic acids) (PLA), carageenans, polystyrene sulfonate, polyamides, polyethylene oxides, cellulose, poly(vinylpyrrolidone) (PVP), poly(vinyl alcohol) (PVA), chitosan, poly(ethyacrylate), methylmethacrylate, chlorotrimethyl ammonium methylmethacrylate, hydroxyapatite, pectin, porcine gastric mucin, poly(sebacic acid) (PSA), hydroxypropyl methylcellulose (HPMC), cellulose acetate phthalate (CAP), magnesium stearate (MS), polyethylene glycol, gum-based polymers such as xanthan gum and its variants, poly-D,L-lactide (PDLL), Kollidon SR (KSR) (a polyvinyl acetate and povidone-based matrix sustained release excipient) and Carbopol 974P NF (carboxypolymethylene), and derivatives of said group. There is provided that the bioerodible polymeric matrix may comprise a compound or composition approved by the Food & Drug Administration of the United States of America.

In a preferred embodiment of the invention there is provided that the bioerodible polymeric matrix may comprise poly(sebacic acid) being an intravaginal microenvironment pH maintenance agent, such that in use, bioerosion of the matrix into its constituent acids and diacid chemical parts facilitates the maintenance of an acidic intravaginal pH impeding sexually transmitted infections and further modulating the release of the pharmaceutical compound from the microspheres.

The bioerodible polymeric matrix may comprise hydroxypropyl methylcellulose, such that in use, said hydroxypropyl methylcellulose facilitates adhesion of the pharmaceutical dosage form to the vaginal mucus lining the vaginal wall, preferably the posterior fornix, by acting as a bioadhesive and/or facilitates binding of the microspheres within the matrix by acting as the binding agent.

The bioerodible polymeric matrix may comprise poly(acrylic acid), such that in use, said poly(acrylic acid) facilitates adhesion of the pharmaceutical dosage form to the vaginal mucus lining the vaginal wall by acting as a bioadhesive.

The bioerodible polymeric matrix may comprise poly(vinylpyrrolidone), such that in use, said poly(vinylpyrrolidone) facilitates binding of the microspheres within the matrix by acting as the binding agent.

The bioerodible matrix may comprise cellulose acetate phthalate and/or derivative thereof, such that in use, said cellulose acetate phthalate and/or derivative thereof modulates bioerosion of the matrix in a pH dependent manner.

The bioerodible matrix may comprise poly-D,L-lactide (PDLL), a hydrophobic polymer, such that in use, said poly-D,L-lactide is the major component of the bioerodible matrix and contributes towards sustained release of the microspheres and in turn the pharmaceutical compound. The poly-D,L-lactide (PDLL) is also an intravaginal microenvironment pH maintenance agent, such that in use, said poly-D,L-lactide degrades through a process of hydrolytic degradation of the ester bonds to form lactic acid which then facilitates the maintenance of an acidic intravaginal pH that impedes sexually transmitted infections or diseases. Further, in use, the poly-D,L-lactide hydrolyzes faster at a higher pH (i.e. when exposed to seminal fluid (of about pH 7.4)) than at a lower pH (i.e. when exposed to normal vaginal fluid (of about pH 4.5)).

The bioerodible matrix may comprise magnesium stearate (MS), such that in use, said magnesium stearate acts as a lubricant to minimise the adhesion of the polymeric matrix to machinery during manufacturing of the dosage form.

The magnesium stearate (MS), also in use, contributes towards matrix hardness wherein an increased amount of magnesium stearate leading to reduced matrix hardness whilst a reduced content of magnesium stearate leading to increased matrix hardness.

Further, in use, the magnesium stearate (MS) is a modifier of microsphere and drug release from the caplet matrix.

The bioerodible matrix may comprise Kollidon SR (KSR) being a blend of poly(vinylpyrrolidone) and poly(vinyl acetate), such that in use, said Kollidon SR acts as a powder binder for the dosage form. The Kollidon SR (KSR), in use, also imparts favourable powder flow properties to the dosage form. Further in use, the Kollidon SR (KSR) contributes to sustained release of the pharmaceutical compound since poly(vinyl acetate) contributes the hydrophobic properties of the polymeric matrix. Still further in use, the Kollidon SR (KRS) provides for good compressibility properties which are mainly contributed the poly(vinyl acetate) part of Kollidon SR.

The Kollidon SR (KSR), in use, also contributes to erosion of the polymeric matrix since the poly(vinylpyrrolidone) part of Kollidon SR is hydrophilic therefore on exposure to an aqueous vaginal environment poly(vinylpyrrolidone) dissolves and leaches out of the polymeric matrix forming holes through which the vaginal fluids may access the interior of the polymeric matrix and the microspheres and pharmaceutical compound may be released. This results in a percolation based release of the microsphere and pharmaceutical compound from the polymeric matrix.

The bioerodible matrix may comprise Carbopol 974P NF, such that in use said Carbopol 974P NF provides for the polymeric matrix to be bioadhesive therein facilitating bioadhesion at the target site. Further, in use, Carbopol 974P NF absorbs vaginal fluid and swells in the aqueous vaginal environment thus modulating release of the pharmaceutical compound.

Furthermore, in use, Carbopol 974P NF contributes toward a pH modulated release of the pharmaceutical compound since at lower vaginal pH of approximately 4.5 the carboxylic groups comprising Carbopol are not ionized and there is normal vaginal fluid uptake and release of the pharmaceutical compound, whilst on exposure to semen pH 7.4 the carboxylic groups comprising Carbopol ionize resulting in their repulsion which in turn leads to increased absorption of the surrounding fluid and an increase in release of the pharmaceutical compound.

In a specific embodiment of the invention, the bioerodible matrix comprises poly-D,L-lactide (PDLL), magnesium stearate (MS), Kollidon SR (KSR) and Carbopol 974P NF.

The pharmaceutical compound may be an antiretroviral, preferably, but not limited to, at least one of the following group: zidovudine, lamivudine, abacavir, lopinavir, ritonavir, emtricitabine, efavirenz and tenofovir. The pharmaceutical compound may be pharmaceutically acceptably salts of antiretrovirals and/or compositions containing antiretrovirals.

The pharmaceutical compound may be a microbicide, preferably, but not limited to, at least one of the following group: kappa carageenan, carbomer, cellulose acetate phthalate, capric acid, polystyrene sulfonate, carageenan, monocaprin, polyacrylic acid, lactobacillus, cellulose sulfate, naphthalene sulfonate, sulfated polyvinyl alcohol, lactic acid, cetyl betaine, myristamine oxide, stampidine, cyanovirin-n, monoclonal antibodies, lyposomes, thrombospondin-1, lime juice, yoghurt, tenofovir, zidovudine, dendrimers, thiourea, silver, polystyrene and sodium lauryl sulfate. The pharmaceutical compound may be pharmaceutically acceptably salts of microbicides and/or compositions containing microbicides.

In an example embodiment of the invention the pharmaceutical dosage form includes an antiretroviral compound and a microbicidal compound. The pharmaceutical compound may comprise several pharmaceutical compounds and/or adjuvants and/or excipients.

The microspheres may have a diameter in the range of about 0.2 to about 0.5 micrometers to facilitate, when used intravaginally, the passage of the microspheres across vaginal mucus lining the target site, the target site located on the vaginal wall.

There is provided for the pharmaceutical dosage form may provide a sustained release of the microspheres from the bioerodible polymeric matrix, and for the microspheres to provide a sustained release of the pharmaceutical compound for at least 24 hours, alternatively 48 hours, from the time microsphere is exposed to the vaginal fluid.

Preferably, the sustained release of the microspheres from the bioerodible matrix and therefore also sustained release of the pharmaceutical compound from the microspheres lasting for a period of approximately 30 days commencing on the day that the dosage form was inserted into the vaginal cavity, preferably the posterior fornix.

In a specific embodiment of the invention wherein the bioerodible matrix comprises poly-D,L-lactide (PDLL), magnesium stearate (MS), Kollidon SR (KSR) and Carbopol 974P NF the sustained release of the microspheres, and in turn the pharmaceutical compound, may be due to hydrolytic degradation of poly-D,L-lactide (PDLL), erosion and through percolation when Kollidon SR (KSR) is leached out of the polymeric matrix. The release mechanism may approximate the Makoid-Banakar model at about pH 4.5 and the Weibull model at about pH 7.4.

In accordance with a second aspect of the invention there is provided a method to produce the pharmaceutical dosage form as described in the first aspect of the invention, the method comprising associating and/or bonding and/or connecting pectin (PEC) with mucin (MUC) in a reaction vessel to form microspheres.

The associating and/or bonding and/or connecting of pectin (PEC) with mucin (MUC) occurs via a crosslinking process wherein a crosslinking agent is employed to facilitate the crosslinking process. In a preferred embodiment of the invention the crosslinking agent may be calcium chloride.

The method may include a further step of adding at least one pharmaceutical compound to the reaction vessel such that each microsphere includes at least one pharmaceutical compound.

The method may include a further step of adding polyethylene glycol (PEG) to the reaction vessel, to produce a PEC-MUC-PEG microsphere as described above in the first aspect of the invention.

The method may include a further step of substantially encapsulating and/or embedding the microspheres within the bioerodible polymeric matrix as described above in the first aspect of the invention, so as to form a pharmaceutical dosage form having a bioerodible polymeric matrix which substantially encapsulates and/or embeds a multitude of microspheres.

The method may include a further step of mechanically shaping and/or dimensioning the pharmaceutical dosage form into a tablet or caplet, in use, the tablet or caplet is inserted into the vagina of a human, preferably within the posterior fornix of the vagina.

In accordance with a third aspect of the invention there is provided for the pharmaceutical dosage form as defined in this disclosure for use in treating a sexually transmitted infection/disease and/or for use in prophylaxis against a sexually transmitted infection/disease comprising intravaginal administration of the pharmaceutical dosage form to a person in need thereof.

In accordance with a fourth aspect of the invention there is provided a method of treating a sexually transmitted infection/disease and/or a method of prophylaxis against a sexually transmitted infection/disease comprising intravaginal administration of the pharmaceutical dosage form as defined in this disclosure.

BRIEF DESCRIPTION OF THE DRAWINGS

Embodiments of the invention will be described below by way of example only and with reference to the accompanying drawings in which:

FIGS. 5 (a) and (b) show transmission electron micrographs of MUC-PEC-PEG microspheres at 40 000× magnification on a JEOL S100 Transmission Electron Microscope;

FIG. 6 show particle size distribution with intensity of optimized PEC-MUC-PEG microspheres;

FIG. 7 shows zeta potential distribution of optimized PEC-MUC-PEG microspheres;

DESCRIPTION OF PREFERRED EMBODIMENTS OF THE INVENTION

Figure 1:
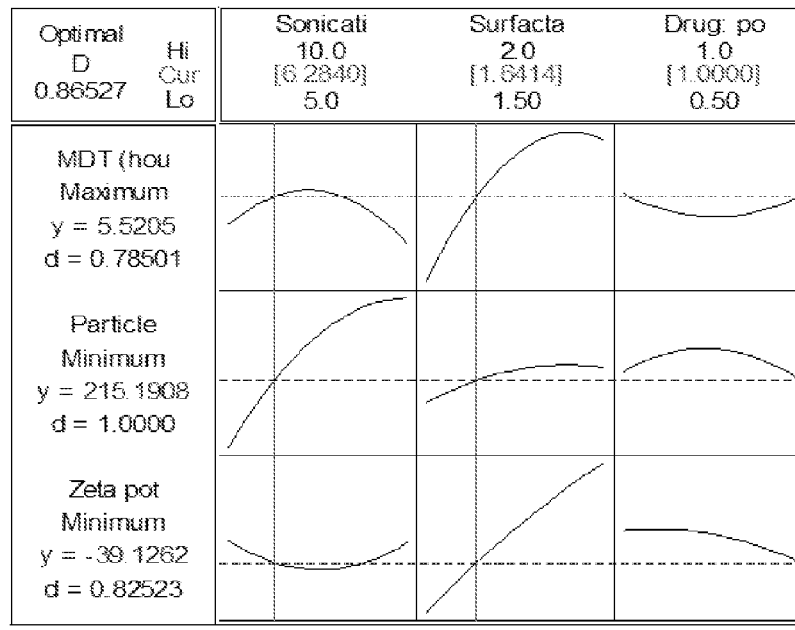
FIG. 1 shows an optimized formulation of a pharmaceutical dosage form in accordance with the first aspect of the invention showing desirability, independent variables and computed responses.

In accordance with a first aspect of this invention there is provided a pharmaceutical dosage form for releasing, at a target site in the vagina of a human, in a controlled and rate modulated manner, a pharmaceutical compound, said pharmaceutical dosage form comprising at least one microparticle, preferably a microsphere, which microsphere comprises a pectin (PEC) framework providing rigidity to the microsphere and porcine gastric mucin (MUC) substantially encapsulated and/or embedded in the pectin framework, such that in use, the at least one PEC-MUC microsphere is inserted into the vagina and the pectin (PEC) and porcine gastric mucin (MUC) modulate release of the pharmaceutical compound at the target site in a pH dependent manner, wherein an increase in pH facilitates an increase in the release rate of the pharmaceutical compound from the microsphere and wherein a decrease in pH facilitates a decrease in the release rate of the pharmaceutical compound from the microsphere.

An alkaline pH facilitates an increase in the release rate of the pharmaceutical compound from the microsphere and an acidic pH facilitates a decrease in the release rate of the pharmaceutical compound from the microsphere.

The PEC-MUC microspheres release the pharmaceutical compound in a pH dependent manner wherein an increase in pH facilitates a conformation change of the porcine gastric mucin (MUC) causing the microsphere's structural integrity to be compromised, in so doing, releasing the pharmaceutical compound. Essentially, the PEC-MUC microspheres release the pharmaceutical compound in a pH dependent manner wherein a decrease in pH facilitates maintenance of the structural integrity of the microspheres such that release of the pharmaceutical compound occurs through diffusion-based means. The release occurring because of the microsphere's structural integrity being compromised is greater relative to release through diffusion-based means.

In a preferred embodiment of the invention the PEC-MUC microspheres additionally include polyethylene glycol (PEG) to form PEC-MUC-PEG microspheres, such that when used intravaginally, the polyethylene glycol (PEG) provides a neutral charge hydrophilic coating for the microsphere, the neutral charge hydrophilic coating facilitating passage of the microspheres across vaginal mucus lining the target site, the target site located on the vaginal wall. The polyethylene glycol (PEG) is typically a low molecular weight polyethylene glycol (PEG), preferably the low molecular weight polyethylene glycol (PEG) having a molecular weight of about 400 g/mol. In an alternative embodiment, the pharmaceutical dosage form may further comprise polyethylene glycol (PEG) such the formed PEC-MUC-PEG microspheres are monolithic in nature, i.e. the PEC, MUC and PEG are blended to form a microsphere, the PEG component of the PEC-MUC-PEG microsphere having a neutral charge and facilitating passage of the PEC-MUC-PEG microspheres across the vaginal mucus lining the target site.

In a particular example embodiment of the invention there is provided for the microspheres to each comprise the pectin (PEC) framework, the porcine gastric mucin (MUC), preferably MUC III, and the low molecular weight polyethylene glycol (PEG), preferably the low molecular weight polyethylene glycol (PEG) having a molecular weight of about 400 g/mol to form PEC-MUC-PEG microspheres. In use the pectin (PEC) facilitates providing rigidity to the microsphere and modulates intravaginal release of the pharmaceutical compound in a pH dependent manner wherein an increase in pH facilitates an increase in release rate of the pharmaceutical compound and wherein a decrease in pH facilitates a decrease in the release rate of the pharmaceutical compound. The pectin (PEC) framework also acts in use to facilitate interpenetration of the microspheres within vaginal tissue located at the target site, and therefore aids in the distribution of the microspheres around the target site. In use the porcine gastric mucin (MUC) modulates intravaginal release of the pharmaceutical compound in a pH dependent manner wherein an increase in pH facilitates an increase in release rate of the pharmaceutical compound and wherein a decrease in pH facilitates a decrease in the release rate of the pharmaceutical compound. The porcine gastric mucin (MUC) also acts in use to facilitate interpenetration of the microspheres within vaginal tissue located at the target site through interaction with inherent mucin of the vagina located at said target site. Further, in use the low molecular weight polyethylene glycol (PEG) provides a neutral charge hydrophilic component or coating for the microspheres, the neutral charge hydrophilic component or coating facilitating passage of the microspheres across vaginal mucus lining the target site, the target site located on the vaginal wall. The polyethylene glycol (PEG) further acts in use to facilitate interpenetration of the microspheres within vaginal tissue located at the target site, and therefore aids in the distribution of the microspheres around the target site.

Typically, a bioerodible polymeric matrix is associated and/or bonded and/or connected with the PEC-MUC microspheres and/or PEC-MUC-PEG microspheres, such that in use, the pharmaceutical dosage form is inserted into the vagina, preferably the posterior fornix, and the bioerodible polymeric matrix erodes over a predetermined time period therein releasing the microspheres which, in turn, release the pharmaceutical compound intravaginally.

The bioerodible matrix is generally substantially hydrophobic and the microspheres substantially hydrophilic, such that release of pharmaceutical compound via diffusion-based means is inhibited. The bioerodible polymeric matrix is selected so as to bioerode at a predetermined rate, therein facilitating the release of the microspheres, the microspheres, in turn, facilitating the release of the pharmaceutical compound to achieve a desired release profile of microspheres and pharmaceutical compound at the target site.

The bioerodible polymeric matrix may comprise an intravaginal microenvironment pH maintenance agent, such that in use, bioerosion of the matrix facilitates the maintenance of an acidic intravaginal pH impeding sexually transmitted infections and further modulating the release of the pharmaceutical compound from the microspheres.

The bioerodible polymeric matrix may have bioadhesive properties, such that in use, the pharmaceutical dosage form adheres to the vaginal wall, preferably in the region of the posterior fornix, alternatively to the surface of the cervix.

The pharmaceutical dosage form may comprise a binding agent to facilitate binding between the bioerodible polymeric matrix and the microspheres.

Generally, as will be explained further below, the pharmaceutical dosage is formed to be a caplet, alternatively a tablet, which caplet or tablet comprises the bioerodible polymeric matrix which substantially encapsulates and/or embeds a multitude of microspheres, such that in use, bioerosion of the matrix results in release of the microspheres which, in turn, releases the pharmaceutical compound. The caplet or tablet is a composite polymeric caplet or tablet.

The bioerodible polymeric matrix comprises a hydrophilic polymer, alternatively a hydrophobic polymer, further alternatively a blend of hydrophilic and hydrophobic polymers, and for the bioerodible polymeric matrix to comprise at least one polymer selected from the group comprising: poly(acrylic acids) (PAA), poly(lactic acids) (PLA), caragreenans, polystyrene sulfonate, polyamides, polyethylene oxides, cellulose, poly(vinylpyrrolidone) (PVP), poly(vinyl alcohol) (PVA), chitosan, poly(ethyacrylate), methylmethacrylate, chlorotrimethyl ammonium methylmethacrylate, hydroxyapatite, pectin, porcine gastric mucin, poly(sebacic acid) (PSA), hydroxypropyl methylcellulose (HPMC), cellulose acetate phthalate (CAP), magnesium stearate, polyethylene glycol, gum-based polymers such as xanthan gum and its variants, poly-D,L-lactide (PDLL), Kollidon SR (KSR) and Carbopol 974P NF, and derivatives of said group. There is provided that the bioerodible polymeric matrix may comprise a compound or composition approved by the Food & Drug Administration of the United States of America.

In a preferred embodiment of the invention there is provided that the bioerodible polymeric matrix comprises poly(sebacic acid) being an intravaginal microenvironment pH maintenance agent, such that in use, bioerosion of the matrix into its constituent acids and diacid chemical parts facilitates the maintenance of an acidic intravaginal pH impeding sexually transmitted infections and further modulating the release of the pharmaceutical compound from the microspheres.

Alternatively or additionally, the bioerodible polymeric matrix comprises hydroxypropylmethylcellulose, such that in use, said hydroxypropylmethylcellulose facilitates adhesion of the pharmaceutical dosage form to the vaginal mucus lining the vaginal wall, preferably the posterior fornix, by acting as a bioadhesive and/or facilitates binding of the microspheres within the matrix by acting as the binding agent.

Further alternatively or additionally, the bioerodible polymeric matrix comprises poly(acrylic acid), such that in use, said poly(acrylic acid) facilitates adhesion of the pharmaceutical dosage form to the vaginal mucus lining the vaginal wall by acting as a bioadhesive.

Even further alternatively, or additionally, the bioerodible polymeric matrix comprises poly(vinylpyrrolidone), such that in use, said poly(vinylpyrrolidone) facilitates binding of the microspheres within the matrix by acting as the binding agent.

Even further alternatively, or additionally, the bioerodible matrix comprises cellulose acetate phthalate and/or derivative thereof, such that in use, said cellulose acetate phthalate and/or derivative thereof modulates bioerosion of the matrix in a pH dependent manner wherein bioerosion of the matrix into its constituent acid and diacid chemical parts facilitates the maintenance of an acidic intravaginal pH impeding sexually transmitted infections and further modulating the release of the pharmaceutical compound from the microspheres.

In a specific preferred embodiment of the invention, the bioerodible matrix comprises poly-D,L-lactide (PDLL), a hydrophobic polymer, such that in use, said poly-D,L-lactide is the major component of the bioerodible matrix and contributes towards sustained release of the microspheres and in turn the pharmaceutical compound. The poly-D,L-lactide (PDLL) is also an intravaginal microenvironment pH maintenance agent, such that in use, said poly-D,L-lactide degrades through a process of hydrolytic degradation of the ester bonds to form lactic acid which then facilitates the maintenance of an acidic intravaginal pH that impedes sexually transmitted infections. Further, in use, the poly-D, L-lactide hydrolyzes faster at a higher pH (i.e. when exposed to seminal fluid (of about pH 7.4)) than at a lower pH (i.e. when exposed to normal vaginal fluid (of about pH 4.5)). It is to be understood that embodiments of the invention are provided for wherein the bioerodible matrix comprises not only poly-D,L-lactide (PDLL) but additionally may include at least one other polymer and/or compound.

Additionally, or alternatively, the bioerodible matrix comprises magnesium stearate (MS), such that in use, said magnesium stearate acts as a lubricant to minimise the adhesion of the polymeric matrix to machinery during manufacturing of the dosage form. The magnesium stearate (MS), also in use, contributes towards matrix hardness wherein an increased amount of magnesium stearate leading to reduced matrix hardness whilst a reduced content of magnesium stearate leading to increased matrix hardness. Further, in use, the magnesium stearate (MS) is a modifier of microsphere and drug release from the caplet matrix.

Further additionally, or alternatively, the bioerodible matrix comprises Kollidon SR (KSR) being a blend of poly(vinylpyrrolidone) and poly(vinyl acetate), such that in use, said Kollidon SR acts as a powder binder for the dosage form. The Kollidon SR (KSR), in use, also imparts favourable powder flow properties to the dosage form. Further in use, the Kollidon SR (KSR) contributes to sustained release of the pharmaceutical compound since poly(vinyl acetate) contributes the hydrophobic properties of the polymeric matrix. Still further in use, the Kollidon SR (KRS) provides for good compressibility properties which are mainly contributed the poly(vinyl acetate) part of Kollidon SR. The Kollidon SR (KSR), in use, also contributes to erosion of the polymeric matrix since the poly(vinylpyrrolidone) part of Kollidon SR is hydrophilic therefore on exposure to an aqueous vaginal environment poly(vinylpyrrolidone) dissolves and leaches out of the polymeric matrix forming holes through which the vaginal fluids may access the interior of the polymeric matrix and the microspheres and pharmaceutical compound may be released. This results in a percolation based release of the microsphere and pharmaceutical compound from the polymeric matrix.

Even further additionally, or alternatively, the bioerodible matrix comprises Carbopol 974P NF, such that in use said Carbopol 974P NF provides for the polymeric matrix to be bioadhesive therein facilitating bioadhesion at the target site. Further, in use, Carbopol 974P NF absorbs vaginal fluid and swells in the aqueous vaginal environment thus modulating release of the pharmaceutical compound. Furthermore, in use, Carbopol 974P NF contributes toward a pH modulated release of the pharmaceutical compound since at lower vaginal pH of approximately 4.5 the carboxylic groups comprising Carbopol are not ionized and there is normal vaginal fluid uptake and release of the pharmaceutical compound, whilst on exposure to semen pH 7.4 the carboxylic groups comprising Carbopol ionize resulting in their repulsion which in turn leads to increased absorption of the surrounding fluid and an increase in release of the pharmaceutical compound.

In a specific embodiment of the invention, the bioerodible matrix comprises poly-D,L-lactide (PDLL), magnesium stearate (MS), Kollidon SR (KSR) and Carbopol 974P NF.

The pharmaceutical compound may be an antiretroviral, preferably, but not limited to, at least one of the following group: zidovudine, lamivudine, abacavir, lopinavir, ritonavir, emtricitabine, efavirenz and tenofovir. The pharmaceutical compound may be pharmaceutically acceptably salts of antiretrovirals and/or compositions containing antiretrovirals.

The pharmaceutical compound may be a microbicide, preferably, but not limited to, at least one of the following group: kappa carageenan, carbomer, cellulose acetate phthalate, capric acid, polystyrene sulfonate, carageenan, monocaprin, polyacrylic acid, lactobacillus, cellulose sulfate, naphthalene sulfonate, sulfated polyvinyl alcohol, lactic acid, cetyl betaine, myristamine oxide, stampidine, cyanovirin-n, monoclonal antibodies, lyposomes, thrombospondin-1, lime juice, yoghurt, tenofovir, zidovudine, dendrimers, thiourea, silver, polystyrene and sodium lauryl sulfate. The pharmaceutical compound may be pharmaceutically acceptably salts of microbicides and/or compositions containing microbicides.

In an example embodiment of the invention the pharmaceutical dosage form includes an antiretroviral compound and a microbicidal compound. The pharmaceutical compound may comprise several pharmaceutical compounds and/or adjuvants and/or excipients.

The microspheres may have a diameter in the range of about 0.2 to 0.5 micrometers to facilitate, when used intravaginally, the passage of the microspheres across vaginal mucus lining the target site, the target site located on the vaginal wall.

There is provided for the pharmaceutical dosage form may provide a sustained release of the microspheres from the bioerodible polymeric matrix, and for the microspheres to provide a sustained release of the pharmaceutical compound for at least 24 hours, alternatively 48 hours, from the time microsphere is exposed to the vaginal fluid.

Preferably, the sustained release of the microspheres from the bioerodible matrix and therefore also sustained release of the pharmaceutical compound from the microspheres lasting for a period of approximately 30 days commencing on the day that the dosage form was inserted into the vaginal cavity, preferably the posterior fornix.

In a specific embodiment of the invention wherein the bioerodible matrix comprises poly-D,L-lactide (PDLL), magnesium stearate (MS), Kollidon SR (KSR) and Carbopol 974P NF the sustained release of the microspheres, and in turn the pharmaceutical compound, may be due to hydrolytic degradation of poly-D,L-lactide (PDLL), erosion and through percolation when Kollidon SR (KSR) is leached out of the polymeric matrix. The release mechanism is closely to follow the Makoid-Banakar model ($R^2$adjusted=0.9973, FIG. 19$b$) at pH 4.5 and the Weibull model ($R^2$adjusted=0.9960, FIG. 19$c$) at pH 7.4.

In accordance with a second aspect of the invention there is provided a method to produce the pharmaceutical dosage form as described in the first aspect of the invention, the method comprising associating and/or bonding and/or connecting pectin (PEC) with mucin (MUC) in a reaction vessel to form PEC-MUC microspheres.

The associating and/or bonding and/or connecting of pectin (PEC) with mucin (MUC) occurs via a crosslinking process wherein a crosslinking agent is employed to facilitate the crosslinking process. In a preferred embodiment of the invention the crosslinking agent may be calcium chloride.

The method may include a further step of adding at least one pharmaceutical compound to the reaction vessel such that each microsphere includes at least one pharmaceutical compound.

The method may include a further step of adding polyethylene glycol (PEG) to the reaction vessel, to produce a PEC-MUC-PEG microsphere as described above in the first aspect of the invention.

The method may include a further step of substantially encapsulating and/or embedding the microspheres within the bioerodible polymeric matrix as described above in the first aspect of the invention, so as to form a pharmaceutical dosage form having a bioerodible polymeric matrix which substantially encapsulates and/or embeds a multitude of microspheres.

The method may include a further step of mechanically shaping and/or dimensioning the pharmaceutical dosage form into a caplet alternatively a tablet, in use, the tablet or caplet is inserted into the vagina of a human, preferably within the posterior fornix of the vagina.

The PEC-MUC-PEG microspheres are suitable for use in intravaginal applications.

The composite PEC-MUC-PEG microspheres are prepared by a crosslinking-emulsion technique which technique is hereby described in general terms below:

A mass of 0.01 g mucin (MUC) is added to 13 mL deionized water whilst stirring at 300 rpm. Stirring continues for 15 minutes before 0.4 g of pectin (PEC) is added and stirred for another 30 minutes. To allow extensive pectin-mucin interpenetration 2 mL of 0.01M calcium chloride (CaCl$_2$), acting as a crosslinking agent, is added drop-wise whilst stirring at 300 rpm for a further 30 minutes. A volume of 0.1 mL of PEG 400 is then added whilst stirring at 300 rpm for 15 minutes to produce the aqueous phase in the emulsion. A water-in-oil (W/O) emulsion is then prepared using a water:oil ratio of 1:4 with the PEC-MUC-PEG crosslinked solution as the aqueous phase and cyclohexane as the oil phase. Span 85 is used as the surfactant. Firstly 1.125 mL of Span 85 is added drop-wise into a beaker containing 60 mL of cyclohexane whilst stirring at 300 rpm for 15 minutes to attain a uniform surfactant distribution. This surfactant-containing cyclohexane is then sonicated at 100% amplitude for 2 minutes using an ultrasonicator whilst adding the PEC-MUC-PEG aqueous solution drop-wise using a syringe to attain a white emulsion. The emulsion is then centrifuged at 4000 rpm for 1 minute to effectively separate the microspheres and the cyclohexane. This results in a white concentrated emulsion remaining at the bottom of the centrifuge tube after decanting cyclohexane. A lyoprotectant such as glucose, mannitol or HP β-cyclodextrin (1% w/v) is added to the concentrated emulsion before freezing the emulsion below (−70° C.) for 24 hours and thereafter lyophilizing it for 48 hours to produce the PEC-MUC-PEG microspheres.

In a preferred embodiment of the invention, the pharmaceutical dosage form is a controlled release intravaginal composite bimodal pharmaceutical dosage form and, more particularly, a composite bimodal polymeric pharmaceutical dosage form wherein the composite comprises PEC-MUC-PEG microspheres, as described above, which are embedded and/or encapsulated within a bioerodible polymeric matrix. Together the microspheres and the matrix are formed into a caplet and/or tablet, such that an outerlayer of matrix substantially encapsulates and/or embeds a multitude of microspheres. The composite bimodal pharmaceutical dosage form is suitable for delivery of a pharmaceutical compound wherein the microspheres carry a pharmaceutical compound and releases said compound in a rate-modulated site-specific manner as the matrix erodes when, in use, the dosage form is administered intravaginally. The dosage form is bimodal as both the matrix and the microspheres have individual functionality which each contributes in providing for rate-modulated site-specific delivery of a pharmaceutical compound.

In order to form the dosage form the PEC-MUC-PEG microspheres are substantially encapsulated and/or embedded with the bioerodible matrix, and then molded and/or shaped and/or dimensioned into a tablet or caplet. The bioerodible matrix should exhibit bioadhesive properties to ensure the dosage form effectively docks to an area inside the vaginal cavity preferably the posterior fornix, alternatively to the surface of the cervix.

The PEC-MUC-PEG microspheres are pH-responsive owing to the individual and combined pH-sensitivity of mucin (MUC) and pectin (PEC). Typically, the MUC is porcine gastric mucin type III, a glycoprotein, which changes its conformational structure depending on the pH of the environment. In acidic pH such as the one found in the normal healthy human vaginal cavity it aggregates, and this helps maintain the microsphere structure when in use. When the pH is high, as in the case when alkaline seminal fluid is introduced to the vaginal cavity during sexual intercourse, mucin (MUC) undergoes conformational transformation into an extended form. The conformational transformation causes the PEC-MUC microspheres or the PEC-MUC-PEG microspheres to lose structural integrity or even to rupture resulting in release of the pharmaceutical compound that can counteract viruses and/or microbes introduced through the semen. Both PEC and MUC are anionic polymers and have carboxylic groups that are not ionized at low or acidic pH. When the pH suddenly changes to alkaline following ejaculation of semen into the vaginal cavity both pectin (PEC) and mucin (MUC) ionize resulting in electrostatic repulsion between the two polymers leading to destabilization and even rupture of the microspheres causing release of the pharmaceutical compound(s) carried by the individual microspheres. The bioerodible matrix typically comprises polysebacic acid which hydrolyzes in the aqueous vaginal environment to sebacic acid thus helping to maintain the desirable acidic vaginal microenviromental pH. Thus the bioerodible matrix acts as a pH maintenance agent helping to maintain an acidic pH in the vagina as it erodes. The maintenance of an acidic pH impedes the transmission of sexually transmitted diseases since acidic pH is detrimental to many pathogenic agents typically causing sexually transmitted diseases. Furthermore, polysebacic acid is hydrophobic hence only the surface aqueous-exposed ester bonds are hydrolyzed in a controlled manner with no pharmaceutical compound leakage from the interior bound microspheres. This results in the microspheres releasing the pharmaceutical compound(s) in a pH responsive way with for at least 24 hours once released from the matrix. Substantially, the release of a pharmaceutical compound from the microsphere may last for up to 24 hours, alternatively 48 hours, from the time that the individual microsphere is released from the matrix.

The pharmaceutical compound(s) included in the PEC-MUC microspheres and/or PEC-MUC-PEG microspheres are typically pharmaceutical compound(s) associated with the treatment and/or prevention of sexually transmitted infections or diseases. More particularly, the pharmaceutical compound(s) are compounds associated with the treatment and/or prevention of HIV/AIDS. It is to be understood that the invention is not limited to pharmaceutical dosage forms for use in the treatment and/or prevention of sexually transmitted diseases and that the microspheres and dosage forms described herein may be utilized in the treatment and/or prevention of other medical and/or physiological and/or biological conditions.

In accordance with a third aspect of the invention there is provided for the pharmaceutical dosage form as defined in this disclosure for use in treating a sexually transmitted infection/disease and/or for use in prophylaxis against a sexually transmitted infection/disease comprising intravaginal administration of the pharmaceutical dosage form to a person in need thereof.

In accordance with a fourth aspect of the invention there is provided a method of treating a sexually transmitted infection/disease and/or a method of prophylaxis against a sexually transmitted infection/disease comprising intravaginal administration of the pharmaceutical dosage form as defined in this disclosure.

The invention as described above provides for a pharmaceutical dosage form which provides for site-specific and rate-modulated intravaginal delivery of a pharmaceutical compound in a pH dependent fashion. The invention at least alleviates one of the problems associated with the prior art.

EXAMPLES

PART 1. Preparation, optimization and characterization of pectin-mucin-polyethylene glycol (PEC-MUC-PEG) microspheres in accordance with the invention.

PART 2. Fabrication of a pharmaceutical dosage form wherein the PEC-MUC-PEG microspheres are formed together with a bioerodible matrix into a composite polymeric caplet.

Part 1: Preparation, Optimization and Characterization of Pectin-Mucin-Polyethylene Glycol (Pec-Muc-Peg) Microspheres for Intravaginal Anti-Hiv-1 Drug Delivery Aim:

To prepare and optimize AZT-loaded PEC-MUC-PEG microspheres.

Materials and Methods

Materials

Porcine gastric mucin type III (MUC III) with 1-1.5% bound sailic acid and polyethylene glycol 400 (PEG $M_w$ 400) were purchased from Aldrich® (Sigma-Aldrich Inc., St. Louis, USA). Commercial grade pectin, GENU® pectin type USP/100 (PEC), [Degree of esterification (DE) 55-65%] was obtained from CP Kelco ApS, Lille Skensved, Denmark. The model anti-HIV-1 active pharmaceutical ingredient (API), zidovudine (AZT) was obtained from Glaxo Smith Kline, Middlesex, UK. Other materials and excipients including; calcium chloride, glucose and cyclohexane were of analytical grade and were utilized as obtained. Simulated vaginal fluid (SVF) was prepared from analytical grade reagents in accordance to Owen and Katz's formulation (*Owen and Katz*, 1999).

Method:

Formulation of AZT Loaded PEC-MUC-PEG Microspheres.

Microspheres where prepared using a crosslinking-emulsion technique. PEC, MUC, PEG and AZT were subsequently dispersed and dissolved in deionised water to form an aqueous phase whilst stirring for 15 min and then crosslinked by drop-wise addition of calcium chloride. A water-in-oil (W/O) emulsion was prepared by ultrasonication with the crosslinked PEC-MUC-PEG-AZT (20% v/v) dispersion as the aqueous phase and cyclohexane as the oil phase. The W:O ratio was 1:4 with span 85 added as the surfactant. The emulsion was centrifuged at 4000 rpm for 1 min and thereafter excess cyclohexane was decanted. The remaining concentrated microsphere emulsion was frozen at −80° C. for 12 hrs before being lyophilized for 48 hrs. Characterization of the microspheres involved: measurement of microsphere particle size, zeta potential using a (Zetasizer Nano ZS, Malvern Instruments Ltd, Worcestershire, United Kingdom) and observation of the shape, appearance and size under a transmission electron microscope (TEM) (JEOL S100 Transmission Electron Microscope, Tokyo, Japan).

Box-Behnken Design Optimization of PEC-MUC-PEG Microspheres

A three-factor, three-level ($3^3$) Box-Behnken statistical design on MINITAB® (V14, State College, Pa., USA) was employed to optimize the AZT-loaded PEC-MUC-PEG microspheres. Upper and lower levels of three independent parameters; ultrasonication time (ST), surfactant concentration (ST) and drug:polymer ratio (D:P ratio) were chosen due to their significance in the fabrication of the microspheres. The responses: particle size, zeta potential mean disillusion time were sought, as presented in Table 1. Fifteen formulations were generated from the Box-Behnken design as presented in Table 2. These formulations were experimentally tested and the results obtained were fed into the software which then computed the optimized formulation.

TABLE 1

Box-Behnken statistical design for PEC-MUC-PEG microsphere optimization

| Independent variables | Levels | |
| --- | --- | --- |
| | Lower | Upper |
| ultrasonication time (min) | 5 | 10 |
| surfactant concentration (% $v/v$) | 1.5 | 2 |
| drug:polymer ratio | 0.5 | 1 |

| Responses | Objective |
| --- | --- |
| particle size (μm) | Minimize |
| zeta potential (mV) | Minimize |
| mean dissolution time (hours) | Maximize |

TABLE 2

Box-Behnken statistical design formulations generated for PEC-MUC-PEG microspheres

| Formulation number | Ultrasonication time (min) | Surfactant concentration (% $v/v$) | Drug:polymer ratio |
| --- | --- | --- | --- |
| 1 | 10 | 1.75 | 0.5 |
| 2 | 10 | 1.5 | 0.75 |
| 3 | 5 | 1.5 | 0.75 |
| 4 | 10 | 2 | 0.75 |
| 5 | 5 | 2 | 0.75 |
| 6 | 7.5 | 2 | 1 |
| 7 | 5 | 1.75 | 1 |
| 8 | 7.5 | 1.75 | 0.75 |
| 9 | 7.5 | 1.75 | 0.75 |
| 10 | 10 | 1.75 | 1 |
| 11 | 7.5 | 1.5 | 0.5 |
| 12 | 5 | 1.75 | 0.5 |
| 13 | 7.5 | 1.5 | 1 |
| 14 | 7.5 | 2 | 0.5 |
| 15 | 7.5 | 1.75 | 0.75 |

Morphological Characterization

The shape and surface morphology of the PEC-MUC-PEG microspheres were observed using a transmission electron microscope (TEM) (JEOL S100 Transmission Electron Microscope (Tokyo, Japan) at 40 000× magnification. The particle size and zeta potential of the microspheres were determined using a Zetasizer (Zetasizer Nano ZS, Malvern Instruments Ltd, Worcestershire, United Kingdom). Microsphere powder (5 mg) was dispersed in 30 mLs of deionized water and passed through a 0.22 μm filter before being used to determine particle size and zeta potential.

Drug Encapsulation and Release

Ultraviolet (UV) absorbance of AZT released from AZT loaded PEC-MUC-PEG microspheres was assessed by measuring UV absorbance of 200 μL aliquot dissolution samples using a nanophotometer (NanoPhotometer™, Implen GmbH, Munchen, Germany) at ambient temperature (25° C.) at lambda max of 267 nm. The dissolution media, simulated vaginal fluid (SVF), was prepared according to Owen and Katz's as in Table 3 (Owen and Katz, 1999). Dissolution was performed using the dialysis membrane technique over 24 hours in 100 mL container filled with simulated vaginal fluid (SVF) and in phosphate buffer PBS. The container was then placed in an orbital shaker incubator (Orbital Shaker Incubator, LM-530D, Yihder Technology CO., LTD, Jhonghe City, Taipei County, Taiwan, Republic of China) at 37° C. rotating at 20 rpm. Aliquots (200 μL) were sampled at predetermined time intervals and Ultraviolet (UV) quantification of the amount of drug released at different time intervals was performed using a nanophotometer (NanoPhotometer™, Implen GmbH, Munchen, Germany). The pH responsiveness of the microspheres was tested by comparing the dissolution profiles in SVF and PBS. Dissolution profiles were generated from the amounts of AZT released these were used to characterize the drug in vitro drug release from the microspheres.

TABLE 3

Vaginal fluid stimulant (VFS) 1 L (Owen and Katz, 1999)

| VFS component | Quantity (g) |
|---|---|
| Sodium chloride (NaCl) | 3.510 |
| Potassium hydroxide (KOH) | 1.400 |
| Calcium hydroxide Ca(OH)$_2$ | 0.222 |
| Bovine serum albumin (BSA) | 0.018 |
| Lactic acid | 2.000 |
| Acetic acid | 1.000 |
| Glycerol | 0.160 |
| Urea | 0.400 |
| Glucose | 5.000 |

The mean dissolution time of AZT from the AZT loaded PEC-MUC-PEG microspheres was calculated according to Equation 1.

$$MDT = \sum_{i=1}^{n} t_i \frac{M_t}{M_\infty} \quad \text{Equation 1}$$

where $M_t$ is the fractional dose released in time $t_i=(t_i+t_{i-1})/2$ and $M_\infty$ corresponds to the loading dose.

Attenuated Total Reflectance Fourier Transform Infrared (ATR-FTIR) Spectrophotometric Analysis:

ATR-FTIR spectra of native PEC, MUC, PEG, AZT and the AZT-loaded PEC-MUC-PEG microspheres were obtained using a Perkin Elmer Spectrum 2000 FTIR spectrometer fitted with a MIRTGS detector (PerkinElmer Spectrum 100, Llantrisant, Wales, UK). Samples were analyzed at a wave number range of 650-4000 cm$^1$ with a resolution of 4 cm$^{-1}$ and 100 scans per spectrum at a direct contact force of 120N. Distinct transmission peaks were used to verify the constitution of the PEC-MUC-PEG microspheres by comparing them to the peaks on the native MUC, PEC, PEG and AZT.

Thermal Analysis Using Differential Scanning Calorimetry (DSC)

Samples of pristine PEC, MUC, AZT and the AZT-loaded PEC-MUC-PEG microspheres were thermally examined by DSC. DSC analysis was conducted employing a differential scanning calorimeter (DSC) (Mettler Toledo, DSC1, STARe System, Schwerzenback, Switzerland) which was calibrated for temperature and enthalpy using indium and zinc. All experiments were performed at a heating rate of 10° C. min$^{-1}$ under a dry nitrogen atmosphere (Afrox, Germiston, Gauteng, South Africa) which flowed at a rate of 200 mLmin$^{-1}$ acting as the purge gas in order to reduce oxidation. Samples were put in 40 μL aluminium pans and heated from −10° C. to 110° C. and kept at 110° C. for 3 minutes. This was done to evaporate any moisture in the sample and to eliminate any thermal history. The samples were then quenched from 110° C. to −10° C. at a rate of 20° C. min$^{-1}$. The midpoint melting point ($T_m$) and heat of fusion (ΔH) which were used for characterization were obtained from the melting point depression of the peaks generated on the experimental DSC curves on heating the samples from −10 to 250° C.

Thermogravimetric Analysis (TGA)

Thermogravimetric measurements were performed on 10-20 mg samples of PEC, MUC, AZT AZ|T-loaded PEC-MUC-PEG microspheres contained in ceramic pans under nitrogen atmosphere using a TGA 4000 thermogravimetric analyzer (Perkin Elmer Inc, Massachusetts, USA). The experiments were run at 10° C.min$^{-1}$ from 50-500° C. Thermograms and their first derivatives obtained for the microspheres and their components were used to determine the thermal degradation properties under a nitrogen atmosphere.

Results and Discussion

Formulation and Optimization of the Microspheres

Figure 2A:
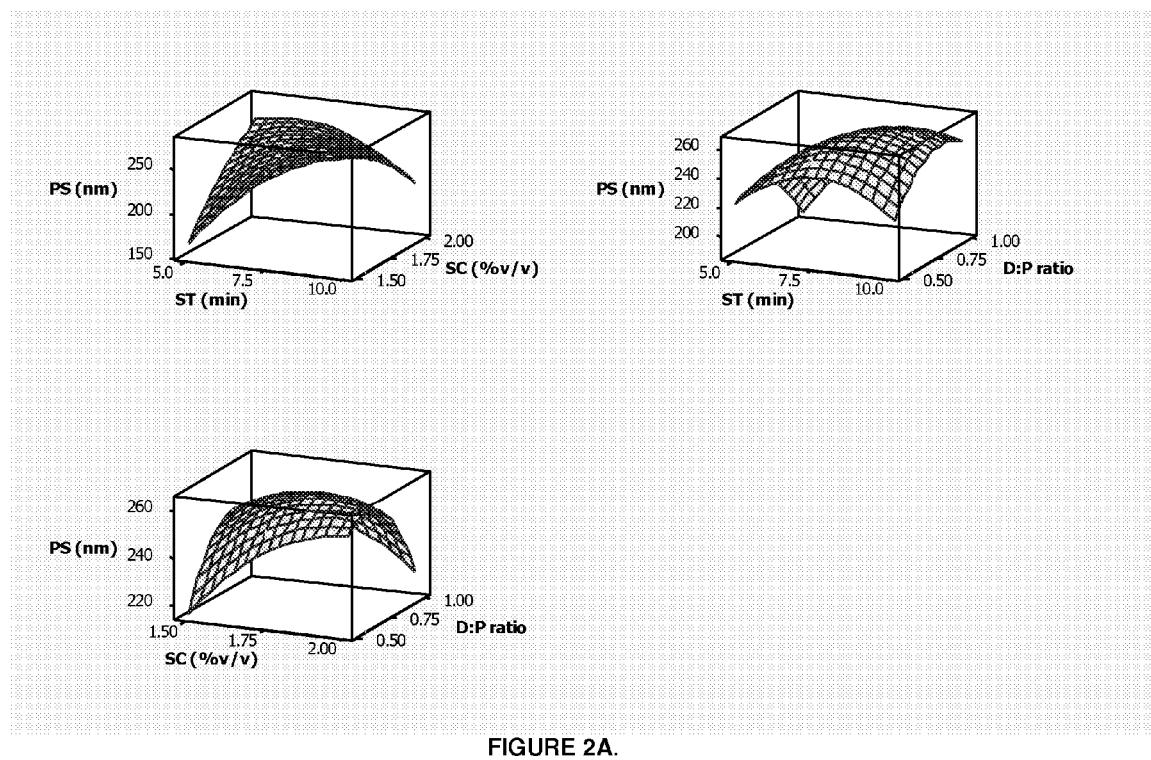
FIG. 2A shows response surface plots correlating independent formulation parameter: particle size (PS) to formulation responses: ultrasonication time (ST), surfactant concentration (SC) and drug:polymer ratio D:P ratio.
Figure 2B:
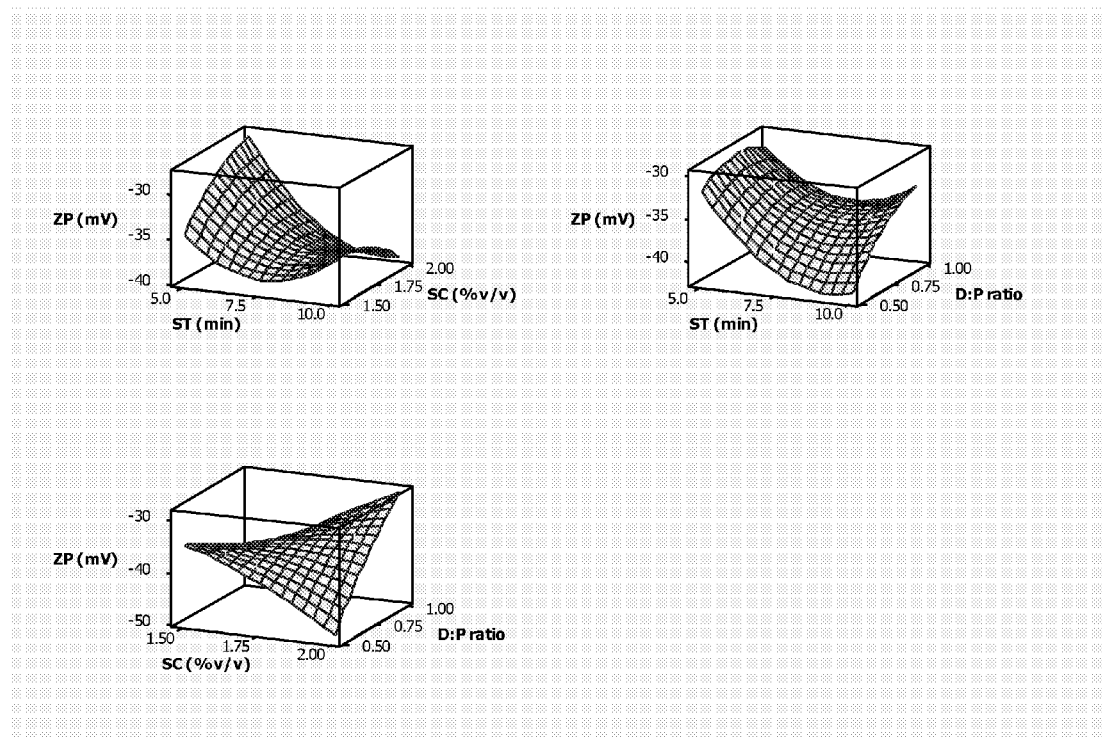
FIG. 2B shows response surface plots correlating independent formulation parameter: zeta potential (ZP) to formulation responses: ultrasonication time (ST), surfactant concentration (SC) and drug:polymer ratio D:P ratio.
Figure 2C:
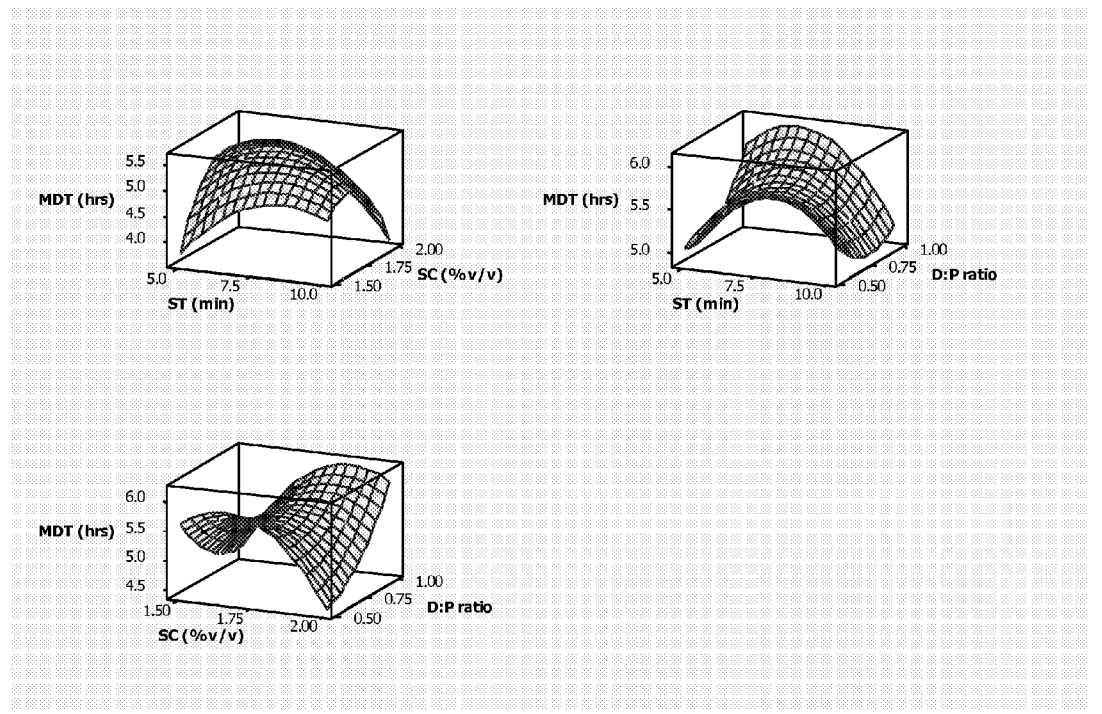
FIG. 2C shows response surface plots correlating independent formulation parameters: mean dissolution time (MDT) to formulation responses: ultrasonication time (ST), surfactant concentration (SC) and drug:polymer ratio D:P ratio.
Figure 3A:
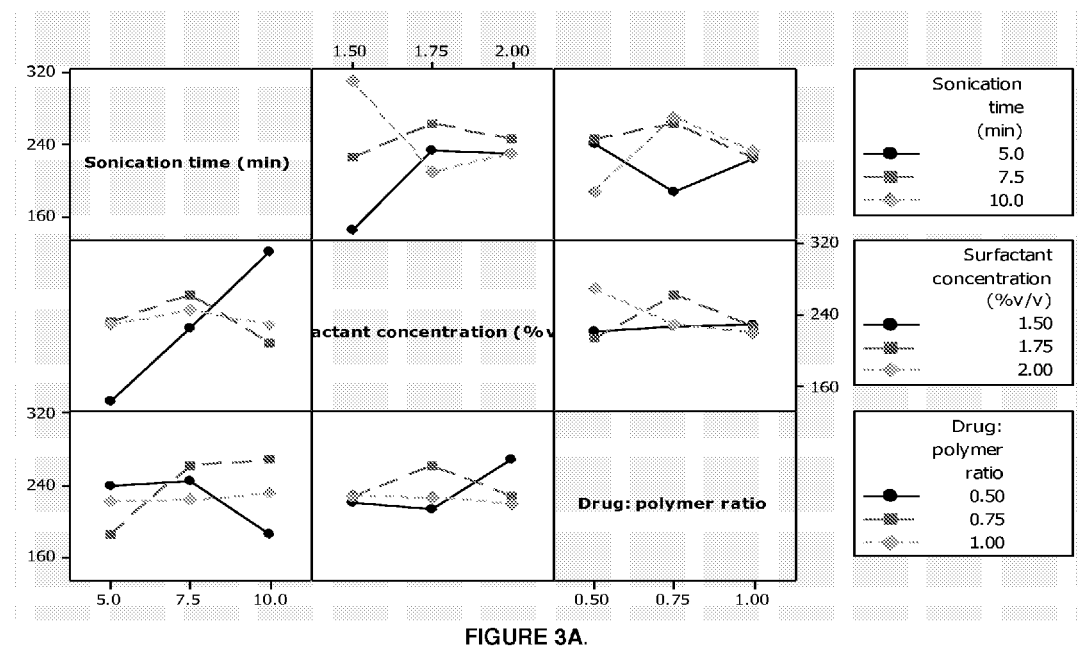
FIG. 3A shows interaction plots of the independent variables that occurred to obtain the particle size response.
Figure 3B:
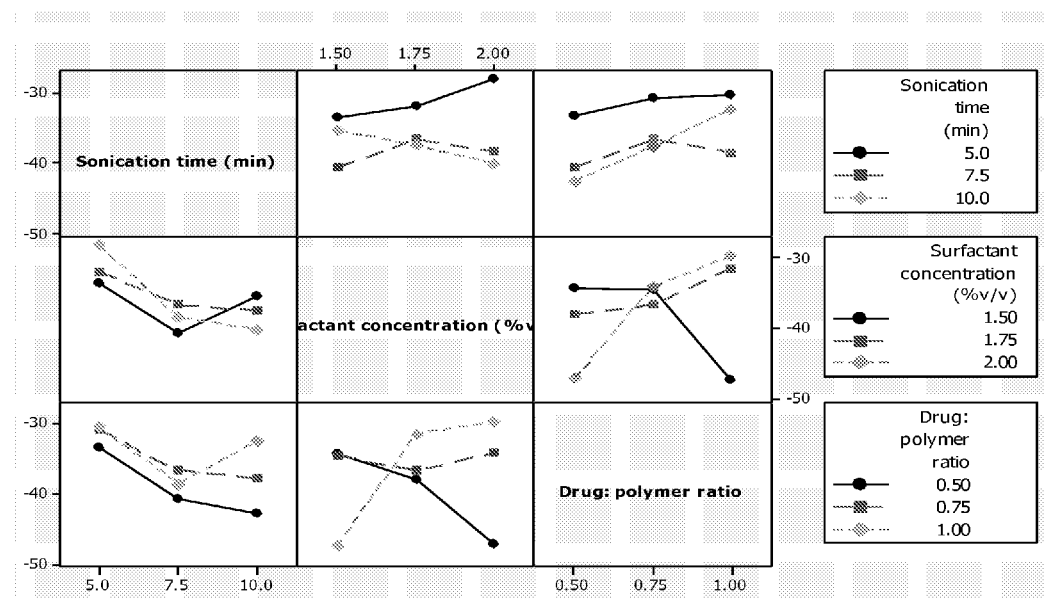
FIG. 3B shows interaction plots of the independent variables that occurred to obtain the zeta potential response.
Figure 3C:
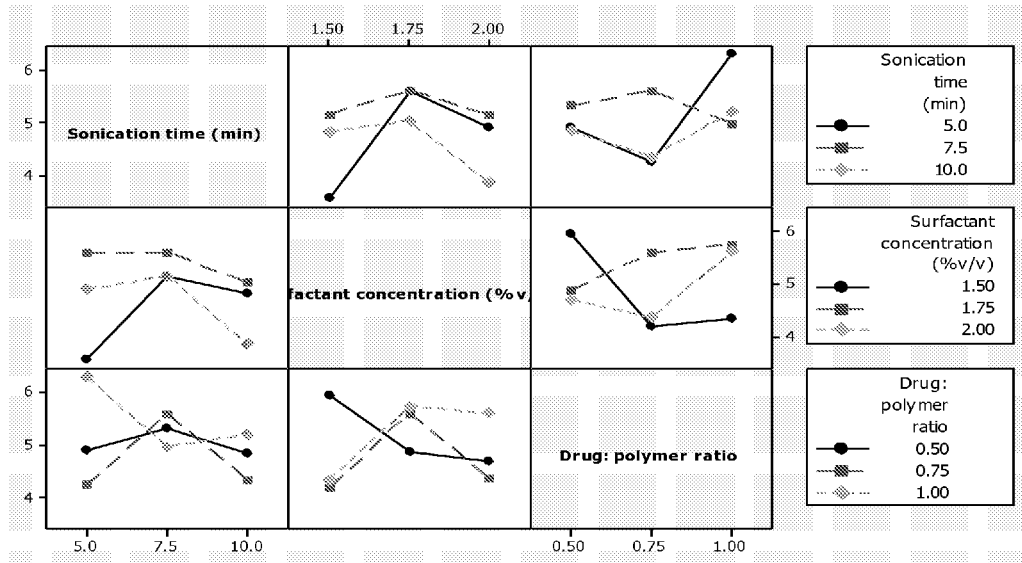
FIG. 3C shows interaction plots of the independent variables that occurred to obtain the mean dissolution time response.
Figure 4A:
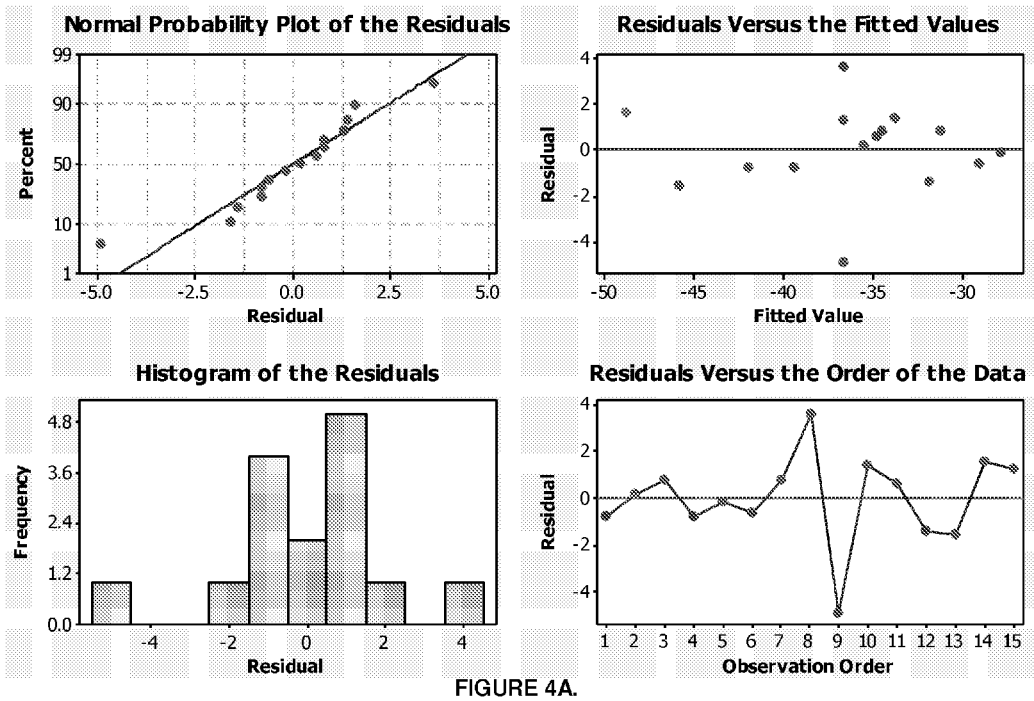
FIG. 4A shows residual plots for particle size determined from the Box-Behnken design of AZT-loaded PEC-MUC-PEG microspheres in accordance with the first aspect of the invention.
Figure 4B:
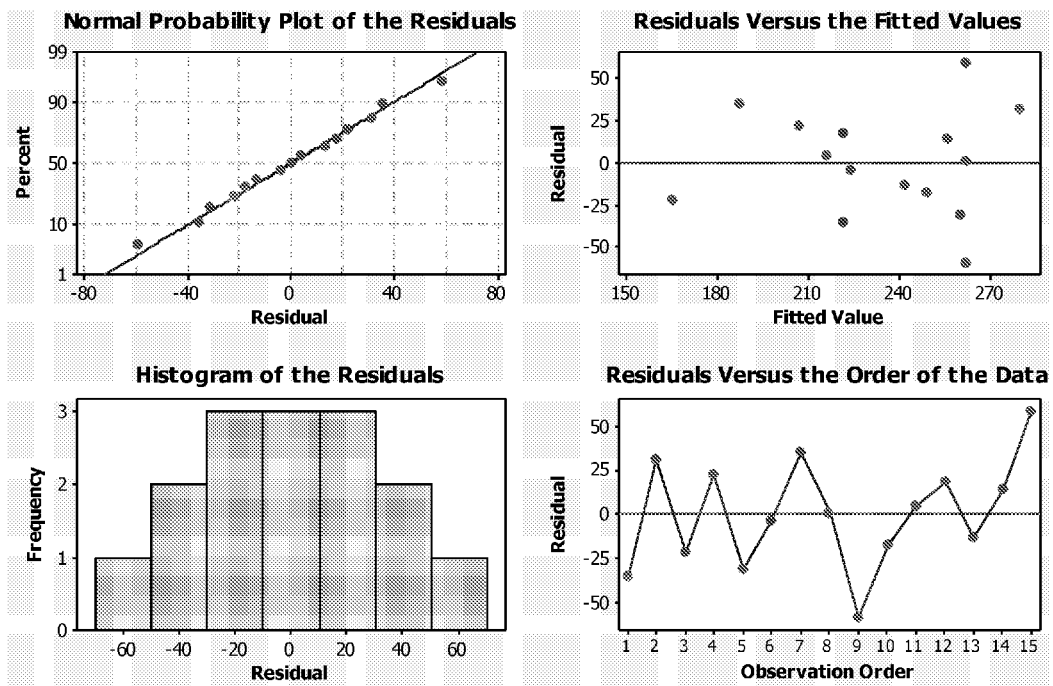
FIG. 4B shows residual plots for zeta potential determined from the Box-Behnken design of AZT-loaded PEC-MUC-PEG microspheres in accordance with the first aspect of the invention.
Figure 4C:
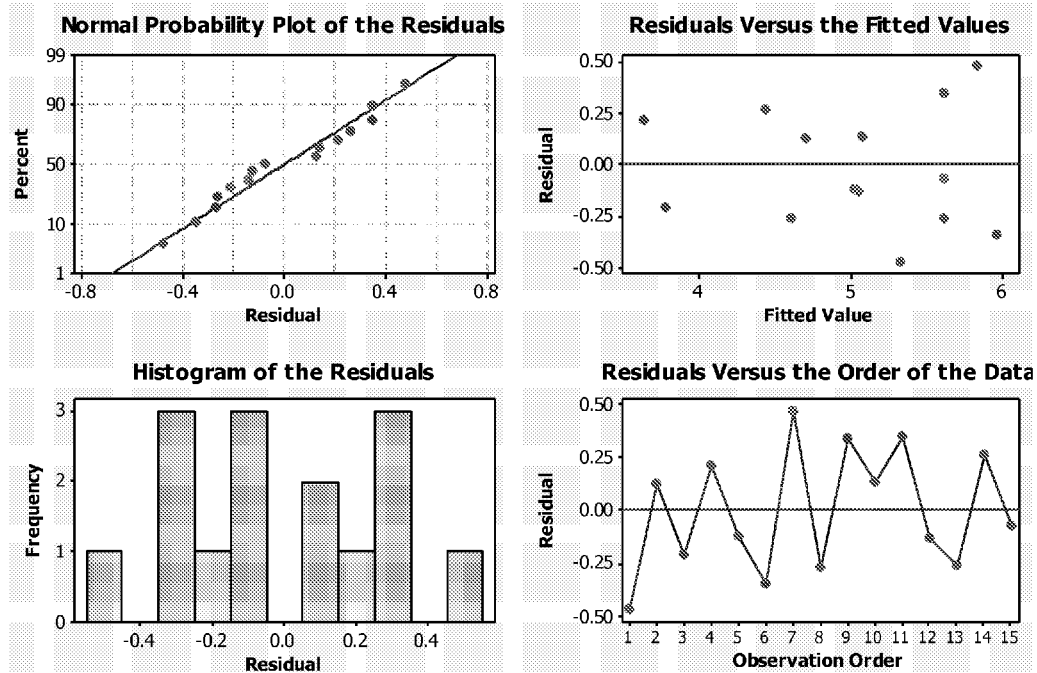
FIG. 4C shows residual plots for mean dissolution time determined from the Box-Behnken design of AZT-loaded PEC-MUC-PEG microspheres in accordance with the first aspect of the invention.

All 15 formulations from the design template produced microspheres of varying particle size, zeta potential and had different mean dissolution times (MDTs) (Table 4). These results were then inputted into the Box Behnken software to yield optimized formulation with independent parameters: ultrasonication time (ST) of 6.28 minutes, surfactant concentration (SC) of (1.64% v/v) and drug:polymer ratio of 1:1 (FIG. 1). These independent parameters yielded computed microspheres of particle size (PS) 215.19 nm, ZP of −39.13 mV and a mean dissolution time (MDT) of 5.52 hours (FIG. 1). The predicted optimized formulation had a desirability of 86.527% (FIG. 1). The correlation of the independent parameters, ultrasonication time (ST), surfactant concentration (SC) and drug:polymer ratio (D:P ratio) to the responses particle size (PS), zeta potential (ZP) and mean dissolution time (MDT) are illustrated as response mesh plots presented in FIGS. 2a-c. How the independent parameters contribute towards the responses observed in the preparation of the microspheres is illustrated by the interaction plots in FIGS. 3a-c and how the formulation responses are distributed in respect of the independent variables are depicted in the different residual plots in FIGS. 4a-c.

TABLE 4

| Formulation number | Particle size (nm) | Zeta potential (mV) | MDT (hours) |
|---|---|---|---|
| 1 | 186.1 ± 4.267 | −42.7 ± 2.350 | 4.852 |
| 2 | 311.0 ± 13.36 | −35.4 ± 0.503 | 4.825 |
| 3 | 143.6 ± 21.11 | −33.7 ± 1.460 | 3.572 |
| 4 | 229.1 ± 52.03 | −40.2 ± 1.400 | 3.845 |
| 5 | 228.7 ± 12.51 | −28.1 ± 0.894 | 4.895 |
| 6 | 220.0 ± 4.768 | −29.7 ± 0.144 | 5.612 |
| 7 | 223.2 ± 12.39 | −30.5 ± 0.193 | 6.300 |
| 8 | 262.9 ± 3.964 | −33.1 ± 0.535 | 5.339 |
| 9 | 203.1 ± 2.989 | −41.6 ± 0.671 | 5.952 |
| 10 | 231.3 ± 4.634 | −32.4 ± 0.618 | 5.209 |
| 11 | 220.6 ± 6.202 | −34.2 ± 0.948 | 5.958 |
| 12 | 239.5 ± 9.255 | −33.3 ± 0.415 | 4.906 |
| 13 | 228.1 ± 5.899 | −47.4 ± 0.536 | 4.349 |
| 14 | 269.3 ± 13.45 | −47.2 ± 0.860 | 4.695 |
| 15 | 321.1 ± 17.37 | −35.4 ± 0.501 | 5.533 |

Morphological Characterization of AZT-Loaded PEC-MUC-PEG Microspheres

Well defined smooth surfaced spherical microspheres were observed under TEM (FIGS. 5a and b). Average particle size for the 15 design formulations ranged from 143.6±21.11 nm to 311.0±13.36 nm with the optimized formulation having an average particle size of 270.6±5.531 nm at a stable polydispersity index (PDI) of 0.303±0.028 as depicted in Table 4 and FIG. 6 respectively. Zeta potential for the 15 design formulations ranged from −28.1 to −47.4 mV as shown in Table 4 with the optimized formulation having a zeta potential of −34.4±0.539 mV signifying that the microspheres were not agglomerated (FIG. 7).

Drug Release from PEC-MUC-PEG Microspheres

Figure 8A:
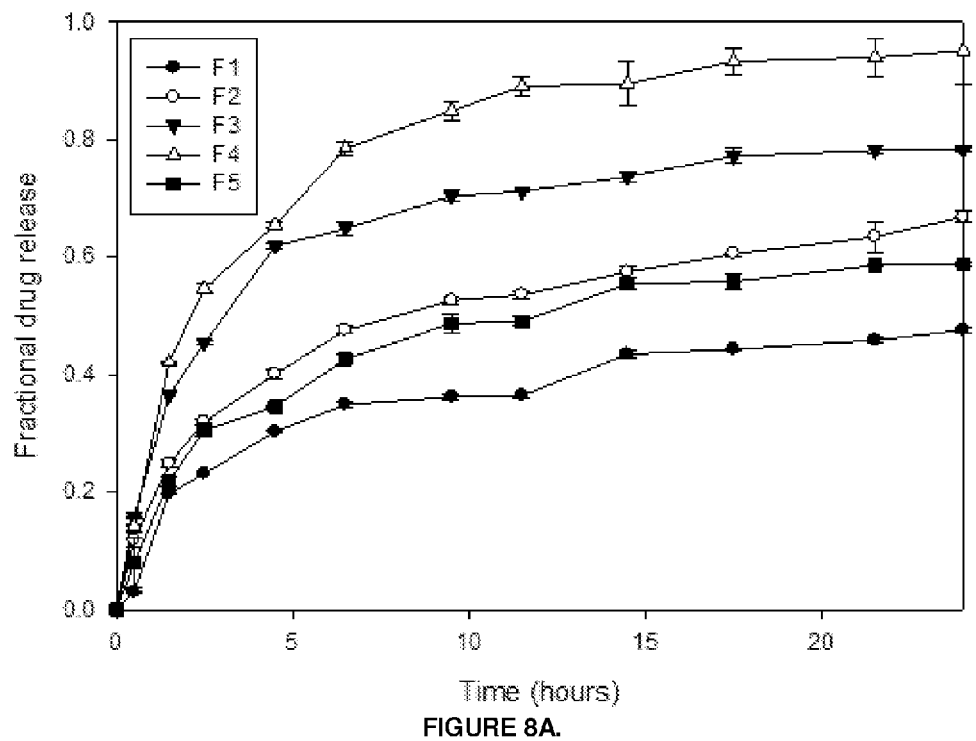
FIG. 8A shows dissolution profiles of formulations F1-F5 in simulated vaginal fluid (SVF) pH 4.5.
Figure 8B:
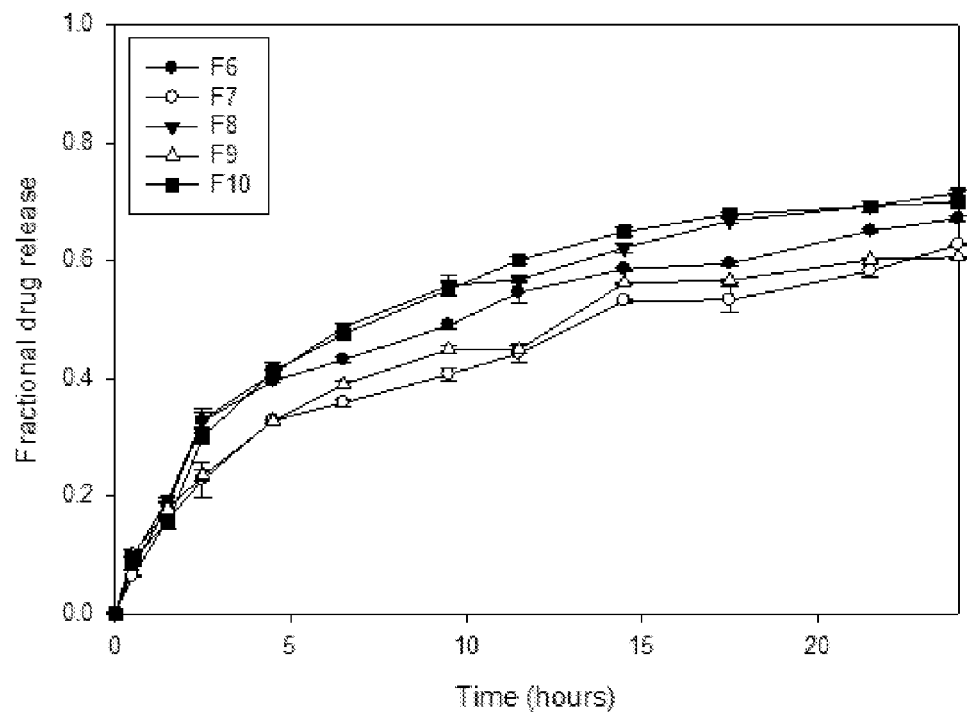
FIG. 8B shows dissolution profiles of formulations F6-F10 in simulated vaginal fluid (SVF) ph 4.5.
Figure 8C:
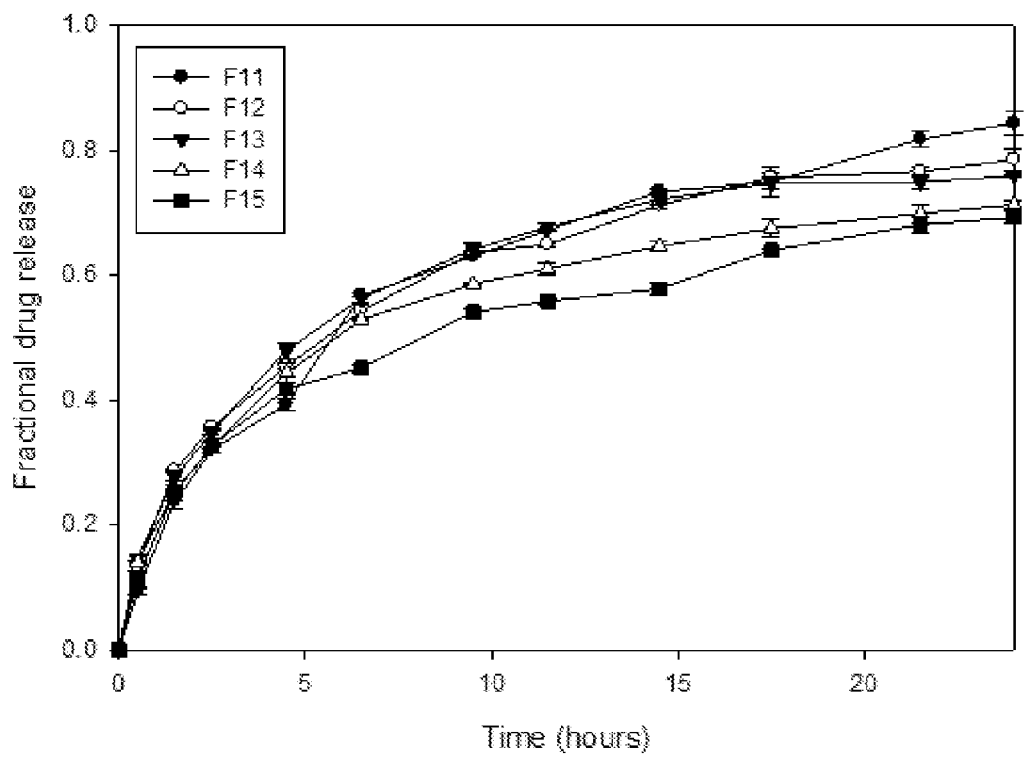
FIG. 8C shows dissolution profiles of formulations F11-F15 in simulated vaginal fluid (SVF) pH 4.5.
Figure 8D:
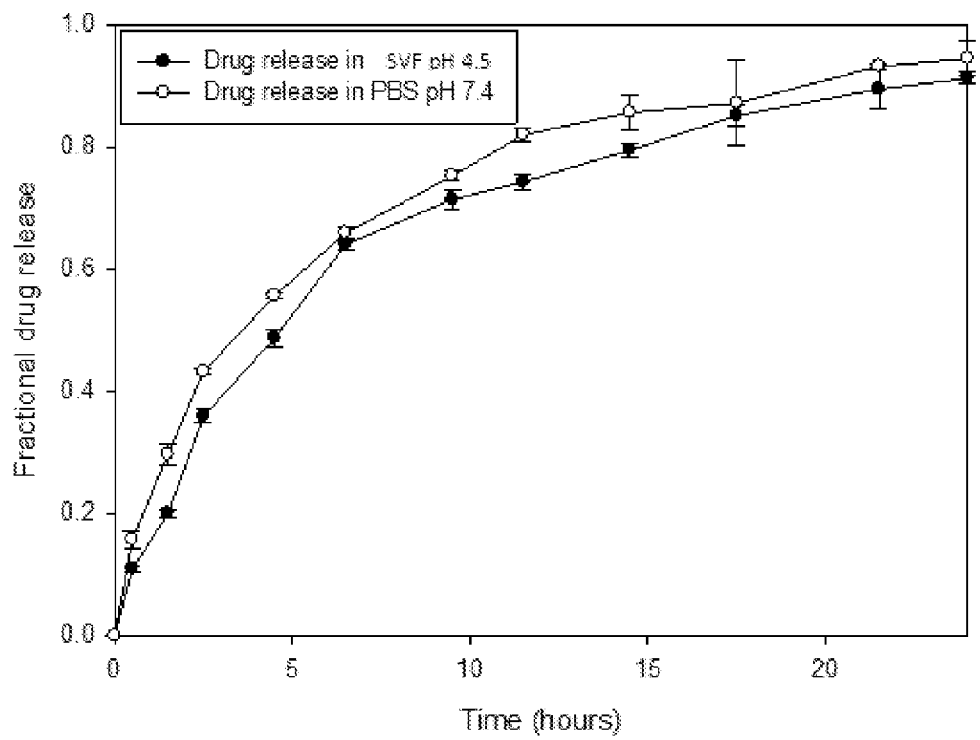
FIG. 8D shows dissolution profiles of the optimized formulation in simulated vaginal fluid (SVF) ph 4.5 and phosphate buffered saline (PBS) pH 7.4.

AZT release from microspheres in SVF occurred mostly within 24 hours for the 15 Box-Behnken design formulations as depicted in FIGS. 8a-d. The ability of the microspheres to retain drug and prevent dissolution was measured by computing the mean dissolution time (MDT). Mean dissolution time (MDT) varied from 3.573 hours for formulation F3 to 6.300 hours for formulation F7 (Table 4). The optimized formulation had a MDT of 5.974 hours. Comparative drug release of the optimized formulation in PBS yielded a MDT of 5.389 hours and its release profile was similar to the one obtained in SVF (FIG. 8d). Drug release from optimized microspheres within 24 hours in SVF pH 4.5 was ~91% as compared to ~94% in PBS (FIG. 8d).

An increase in pH from acidic (pH 4.5 SVF) to alkaline (pH 7.4 PBS) caused a destabilization in the architecture of the microspheres leading increased leakage of the encapsulated drug as shown by the increase in the fractional release in PBS as compared to that seen in SVF in FIG. 8d. Additionally, the mean dissolution time for the drug to be released from the microspheres was shorter in PBS as compared to SVF as in Table 4. This variation in drug release in different media pH may be explained by the presents of carboxyl groups in pectin (PEC) and mucin (MUC) which are neutral in acidic pH and which are then ionized in alkaline pH thus causing repulsive destabilization of the microspheres thereby leading to increased drug release and a decreased mean dissolution time.

Figure 9A:
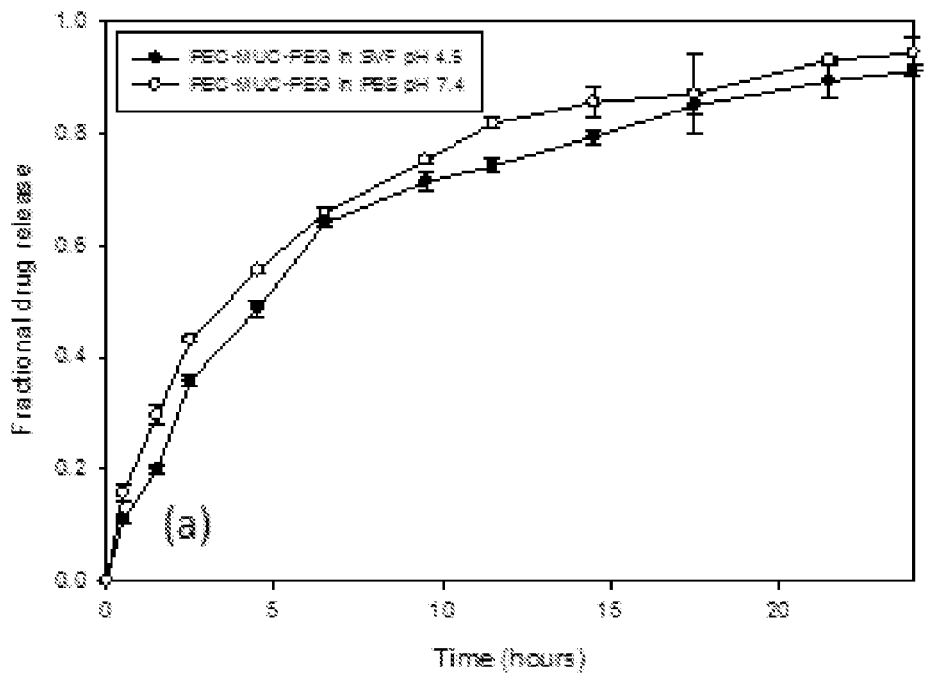
FIG. 9A shows comparison of AZT release from loaded PEC-MUC-PEG microspheres in SVF pH 4.5 to AZT release from PEC-MUC-PEG microspheres in PBS pH 7.4.
Figure 9B:
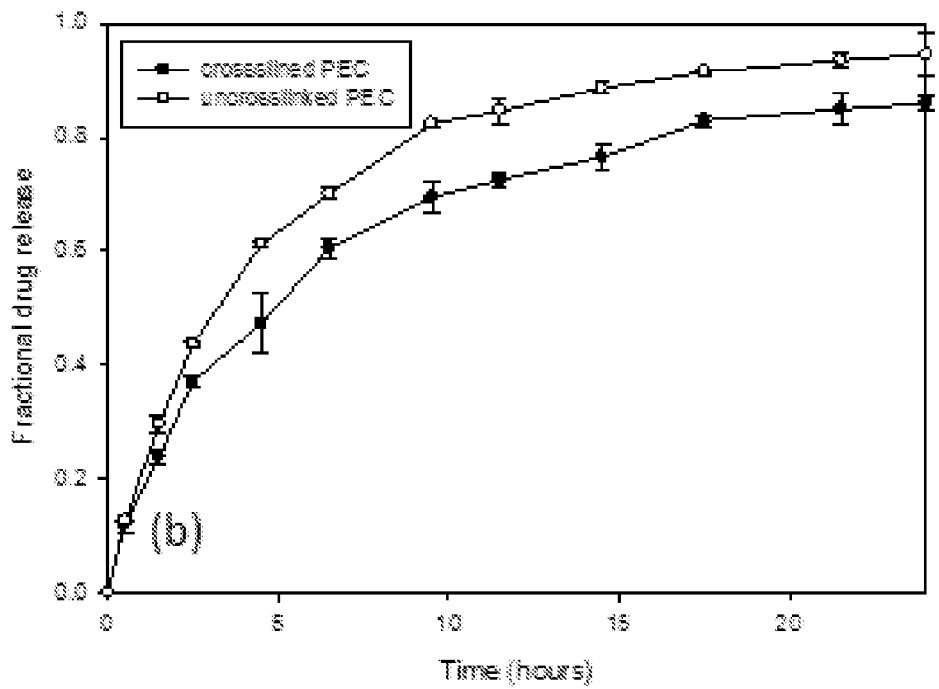
FIG. 9B shows comparison of AZT release from loaded crosslinked PEC microspheres to release from uncrosslinked PEC microspheres both in SVF.
Figure 9C:
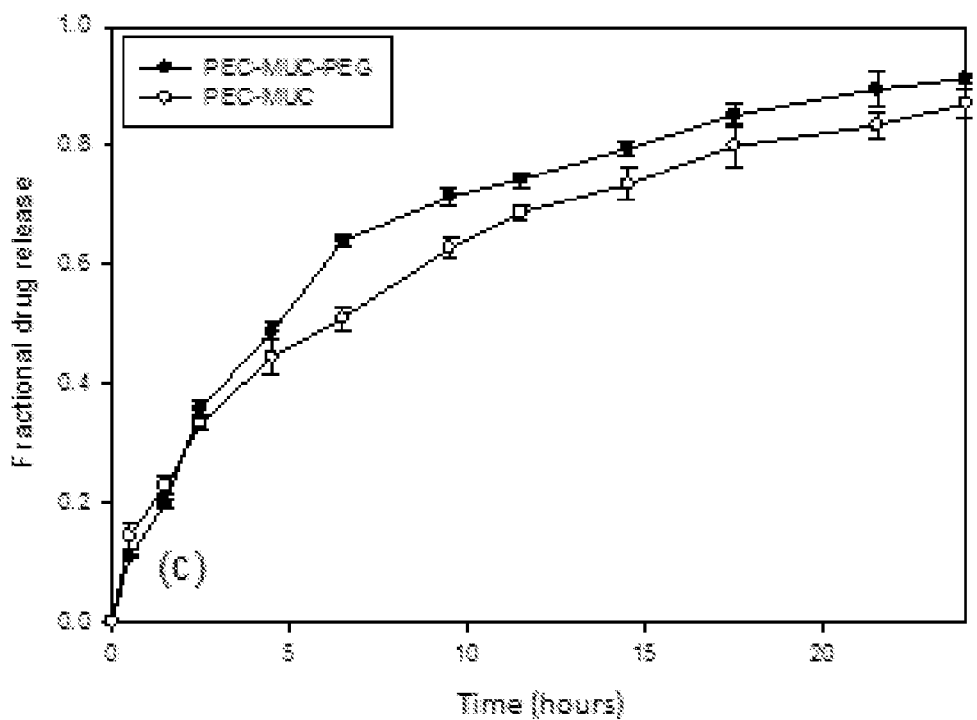
FIG. 9C shows comparison of AZT release from loaded PEC-MUC-PEG microspheres to release in PEC-MUC microspheres in SVF.
Figure 9D:
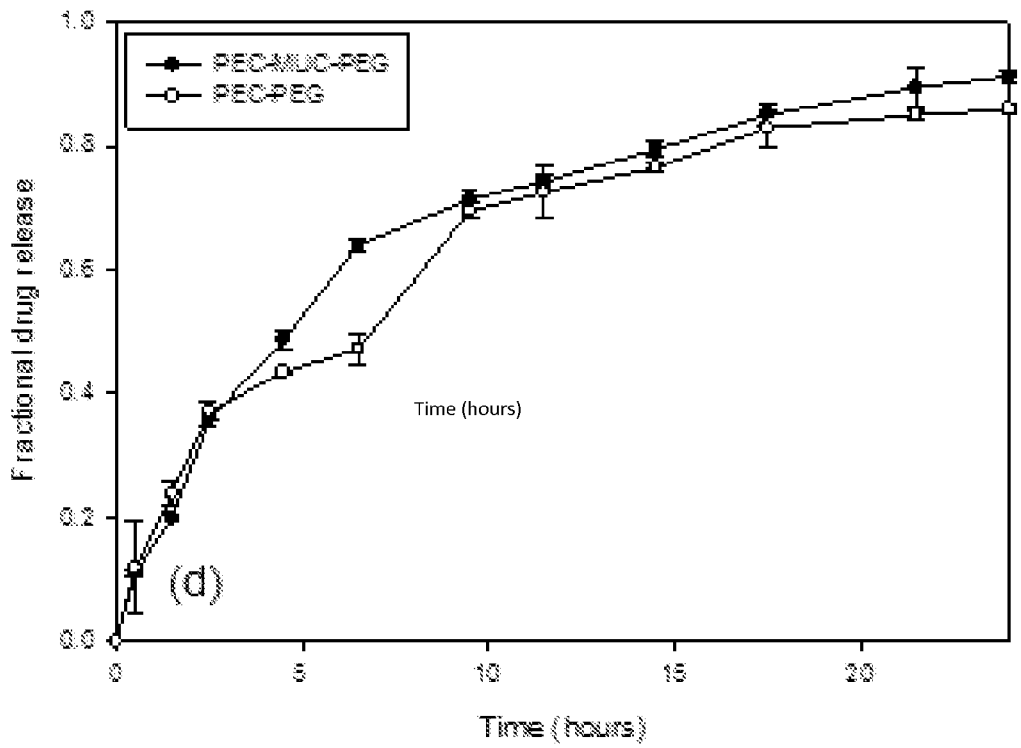
FIG. 9D shows comparison of AZT release from loaded PEC-MUC-PEG microspheres to release in PEC-PEG microspheres.
Figure 10:
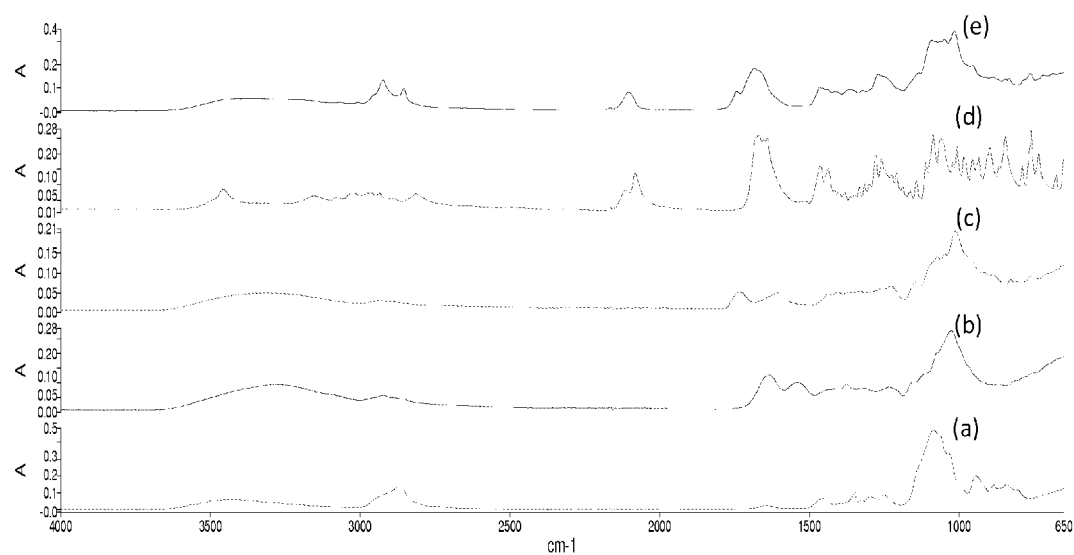
FIG. 10 shows ATR-FTIR spectra of: (a) PEG, (b) MUC, (c) PEC, (d) AZT, and (e) AZT-loaded PEC-MUC-PEG.

From the dissolution profiles in FIG. 9b, it was noted that crosslinking PEC reduced the amount of drug released in 24 hours. PEG caused a light increase in drug released as it draws water molecules towards the microspheres my forming hydrogen bonds (FIG. 9C). MUC did not make a major effect on release in SVF (FIG. 9d).

ATR-FTIR Analysis of PEC, MUC, PEG, AZT and AZT-Loaded PEC-MUC-PEG

FTIR Spectrum of AZT-loaded PEC-MUC-PEG microspheres revealed the drug and macromolecular composition of the microspheres with significant peaks being observed at; 2104.53 cm$^{-1}$ which was a result of the contribution from AZT, 2923.68 cm$^{-1}$ which was contributed by PEG, the peak at 3384.56 cm$^{-1}$ which resulted from the stretching vibrations of the carboxylic and hydroxyl groups found in PEC, MUC and PEG (FIG. 10a-e).

PEC-MUC-PEG
Differential Scanning Calorimetric (DSC) Analysis

Figure 11:
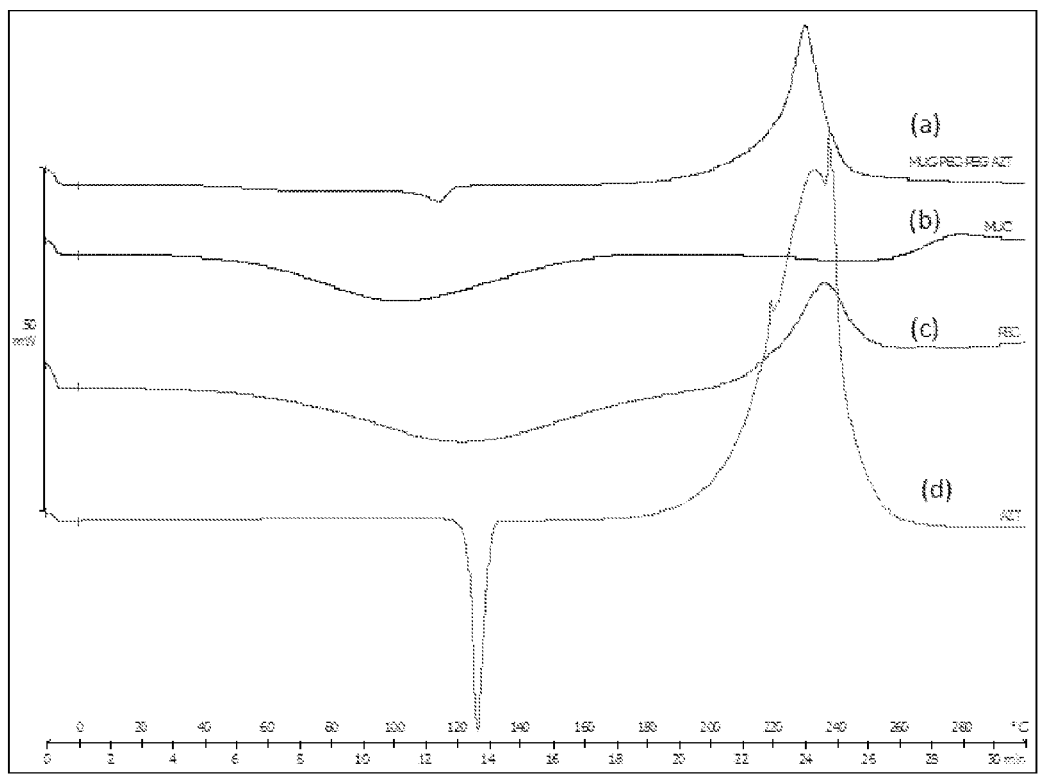
FIG. 11 shows DSC thermograms of (a) AZT-loaded PEC-MUC-PEG (b) MUC (c) PEC (d) AZT.

DSC thermograms of AZT-loaded PEC-MUC-PEG microspheres, MUC, PEC and AZT are depicted in FIG. 11. AZT-loaded PEC-MUC-PEG microspheres had a broad endothermic peak representing the melting point at a peak maxima at 113.67° C. with a measured heat of fusion equal to 9.75 Jg$^{-1}$ and an exothermic crystallization peak at 230.81° C. (FIG. 11a). Microsphere components: MUC had an melting point represented by an endothermic peak maxima at 101.36° C. (FIG. 11b), PEC had a melting endothermic peak at 120.73° C. as well as an exothermic crystallization peak at 236.17° C. (FIG. 11c) and the model drug, AZT, had an onset melting point at 122.88° C. and an exothermic crystallization peak at 240.34° C. FIG. 11d.

Figure 12A:
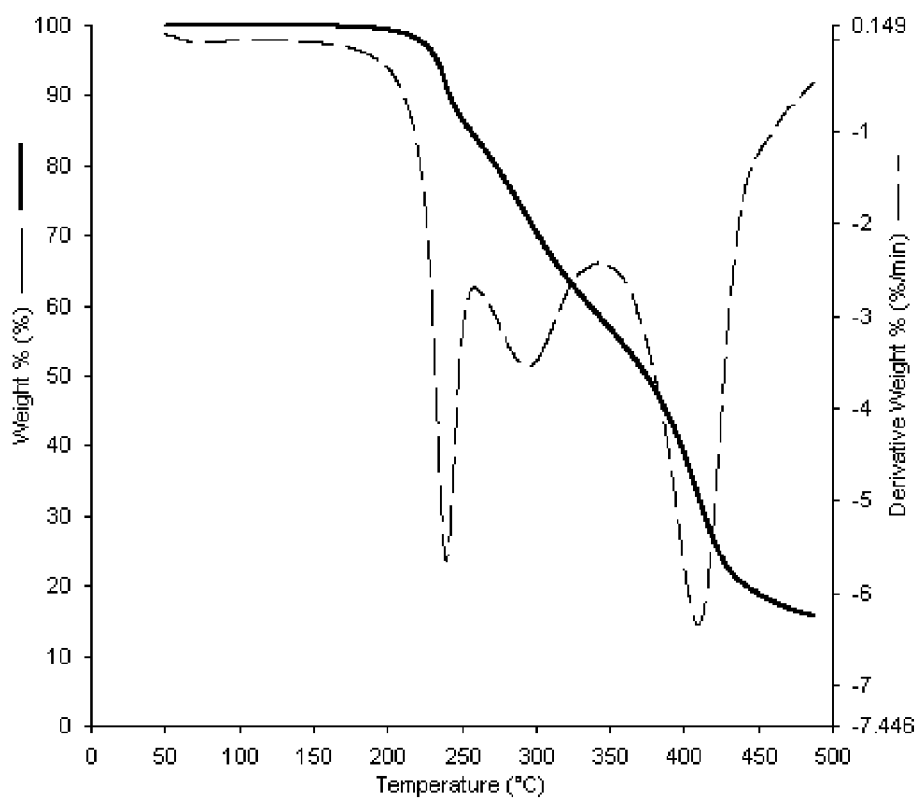
FIG. 12A shows TGA (solid) and DTGA (dotted) thermograms of AZT-loaded PEC-MUC-PEG.
Figure 12B:
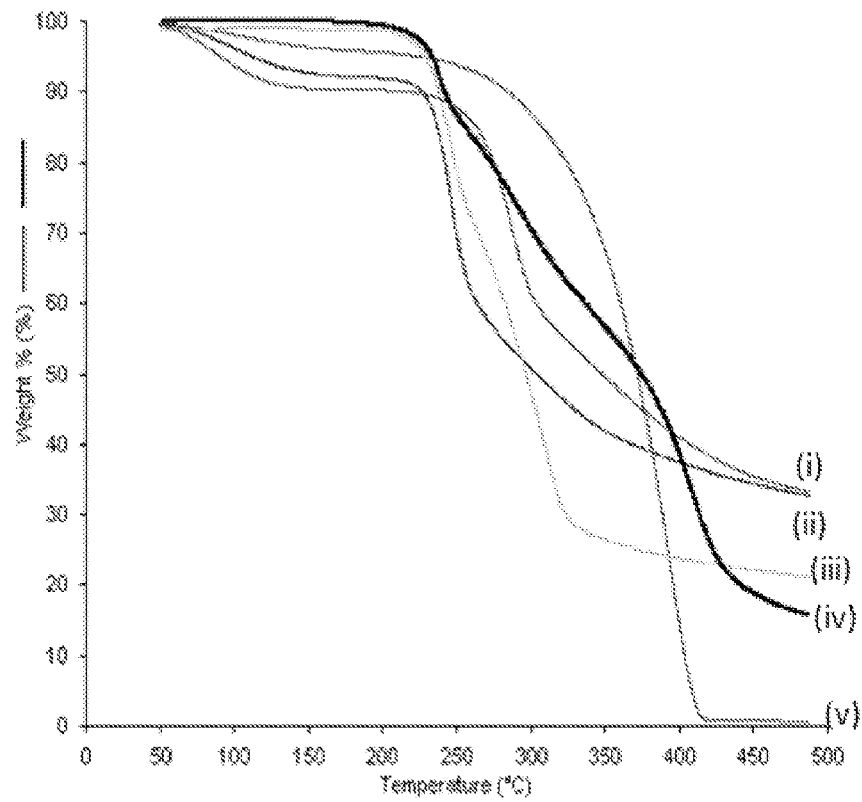
FIG. 12B shows TGA thermograms of: (i) MUC, (ii) PEC, (iii) AZT, (iv) AZT-loaded PEC-MUC-PEG microspheres, and (v) PEG.
Figure 12C:
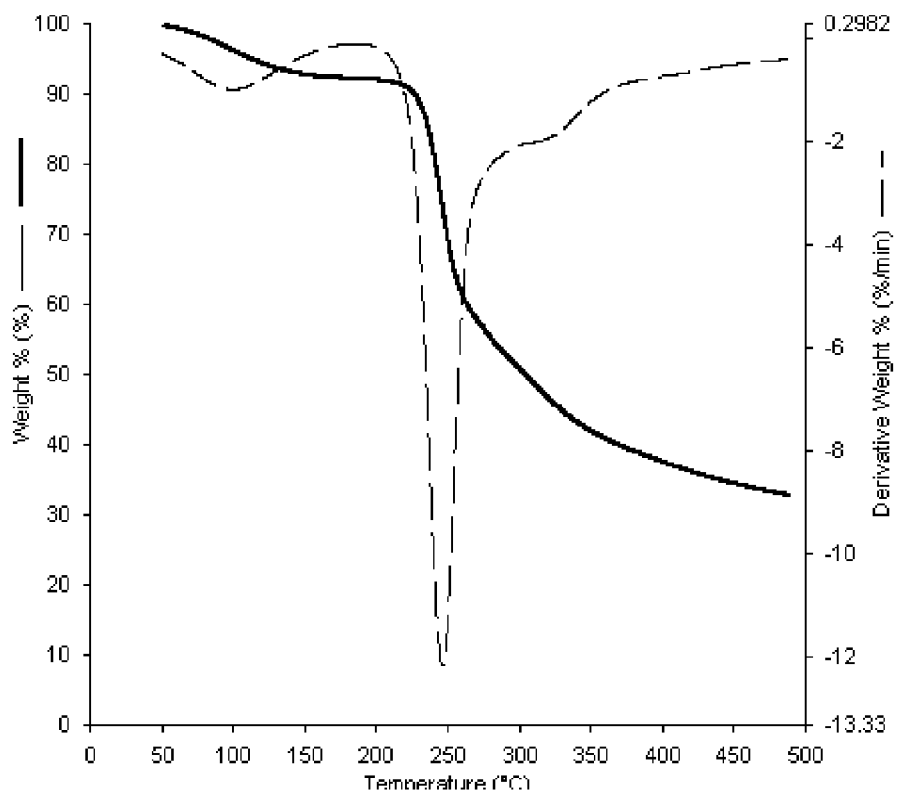
FIG. 12C shows TGA (solid) and DTGA (dotted) thermograms of PEC.

Thermogravimetric Analysis (TGA) of AZT Loaded PEC-MUC-PEG Microspheres and their Native Constituents The thermal degradation of AZT-loaded PEC-MUC-PEG microspheres as measured by TGA produced the thermogram depicted in FIG. 12a. The microsphere TGA thermogram depicts indistinctive one-step degradation with weight loss of approximately 84% on heating from 50-500° C. However, its first derivative TGA (DTGA) revealed that the microspheres degraded in three major steps represented by peaks at 239.60° C., 287.90° C. and 409.77° C. that correspond to the points of inflection on the TGA thermogram. It is important to compare the microsphere TGA thermogram with that of all the components from which the microspheres were formulated which are depicted in FIG. 12b. FIG. 12c depicts the TGA and DTGA thermograms of PEC. Thermal degradation of PEC was shown to take place in two steps; the first was a minor step that took place from 50-150° C. resulting in 7.919% weight loss and point of inflection at 95.03° C. which may have been a result of dehydration and then the major second degradation step which had an extrapolated onset and end at 233.54° C. and 276.92° C. respectively with its point of maximum degradation represented by the DTGA (peak 246.01° C.). This second degradation step resulted in a weight loss of approximately 59% and was most likely due to the depolymerization of PEC carbohydrate chains (Kumar et al., 2010). PEC weight loss of approximately 66.98% was experienced from 50-500° C. The first DTGA peaks of the microspheres (239.60° C.) and PEC (246.01° C.) were close therefore; PEC degradation might have contributed to the initial degradation of the microspheres.

Figure 12D:
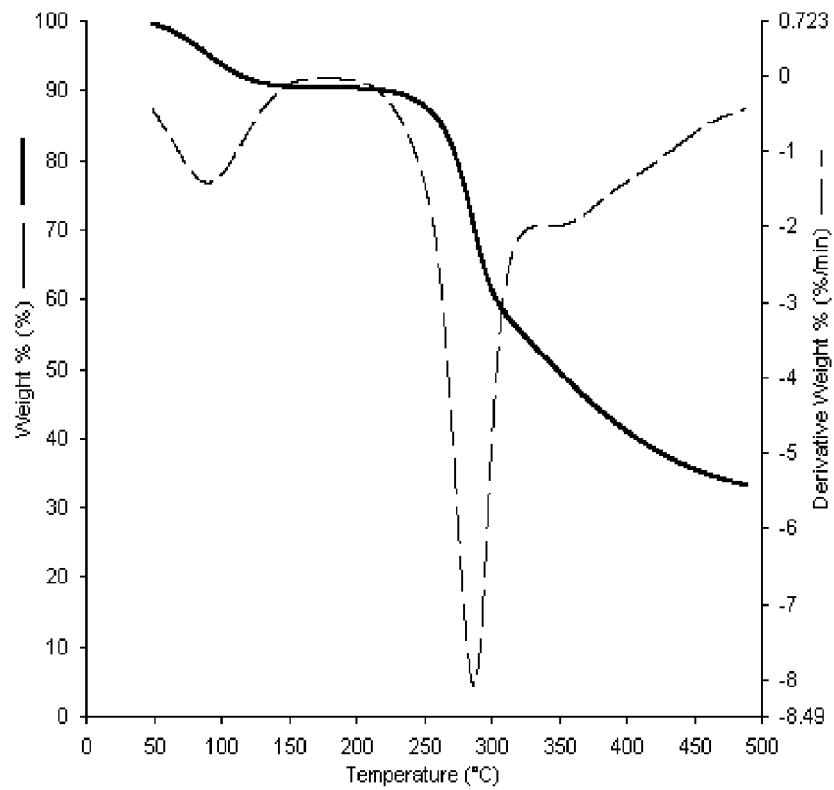
FIG. 12D shows TGA (solid) and DTGA (dotted) thermograms of MUC.

Thermal degradation of MUC was observed to occur in two steps, with the first minor step occurring from 50-150° C. with a corresponding DTGA peak at 90.63° C. resulting in a weight loss of approximately 9.14% (FIG. 12d). This step was likely a result of the evaporation of bound water. It was then followed by a major degradation step with an extrapolated onset and end at 264.58° C. and 330.64° C. respectively with its point of inflection corresponding to the DTGA peak at 286.50° C. This major degradation step might have been a result of the oligosaccharide side chain depolymerization. There was a total weight loss of 66.17% on heating MUC from 50-500° C. Due to the closeness of the DTGA pecks of the second degradation steps, MUC (peak at 286.50° C.) and microspheres (peak at 287.90° C.), MUC might have contributed to the degradation of the microspheres.

Figure 12E:
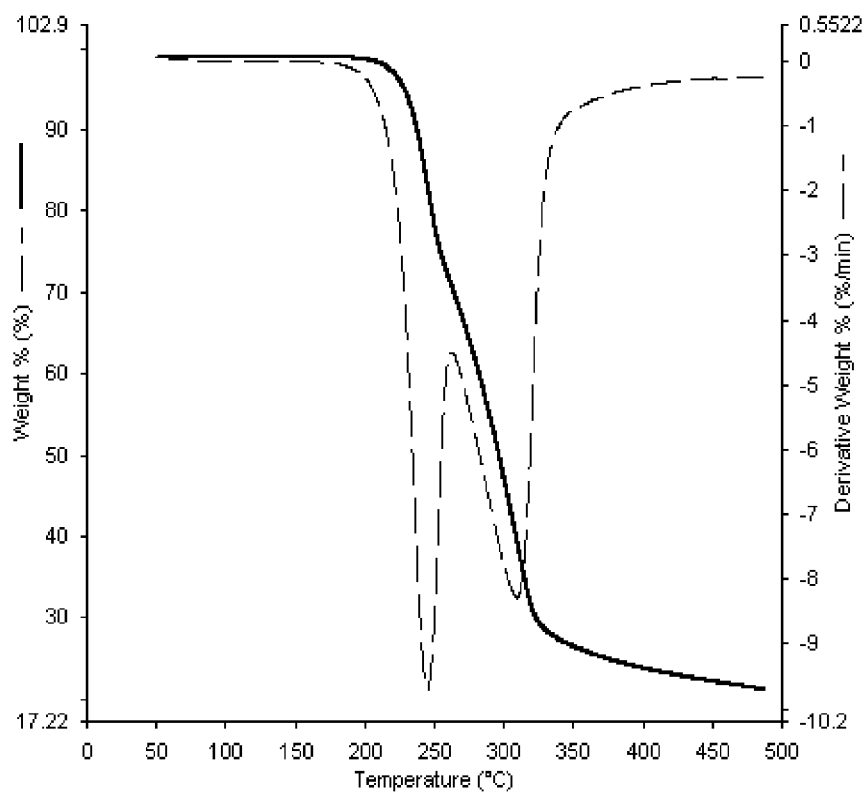
FIG. 12E shows TGA (solid) and DTGA (dotted) thermograms AZT.
Figure 12F:
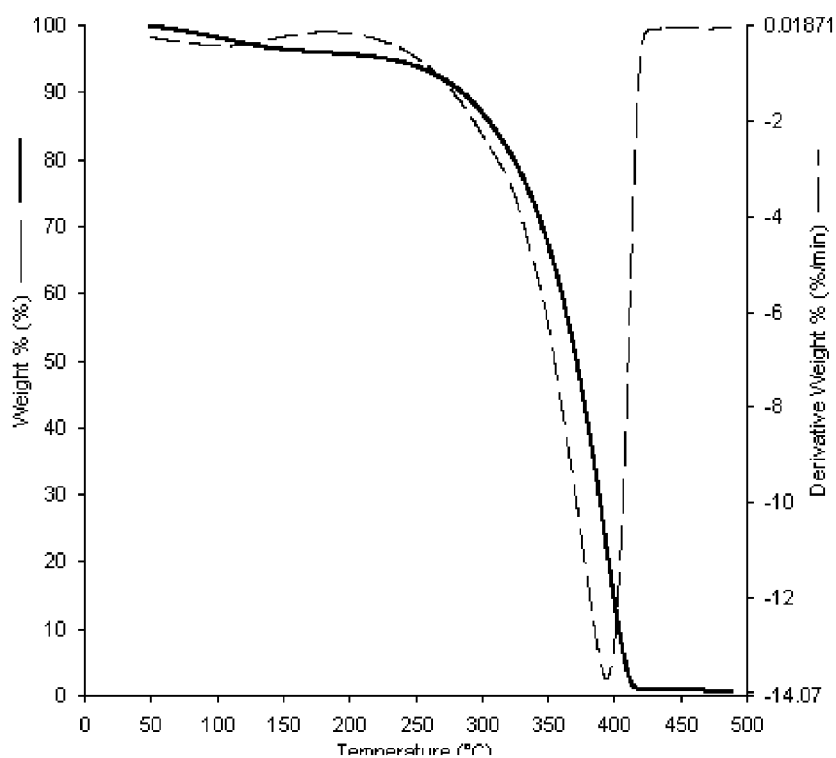
FIG. 12F shows TGA (solid) and DTGA (dotted) thermograms of PEG.

The encapsulated drug, AZT, thermally degraded in two steps depicted by the DTGA peaks at 244.10° C. (first step) and 310.70° C. (second step) which might have contributed to the first and second step of the microsphere degradation steps (FIG. 12e). Degradation of AZT started at the extrapolated beginning of 230.14° C. then the second degradation step began before the first degradation step ended. The extrapolated end of the degradation of AZT was at 331.48° C. and the total AZT weight loss on heating from 50-500° C. was 77.935%. The third degradation step of the microspheres (DTGA peak 409.77° C.) was likely due to the degradation of PEG which degraded almost completely (99.084%) in a major step with an extrapolated onset and end of 338.89° C. and 393.97° C. respectively (FIG. 12f). The point of maximum degradation of PEG corresponds to the DTGA peak at 395.15° C.

All the three degradation steps of the PEC-MUC-PEG microspheres were shifted to the right as compared to the corresponding degradation steps of the respective components of the PEC-MUC-PEG microspheres and this suggests that the microspheres were thermally stable. The thermal stability might have been brought about by the crosslinking technique used in formulation of the microspheres as well as the intermolecular interactions possibly due to hydrogen bonding of the carboxyl, hydroxyl and amine groups in PEC, MUC, PEG and AZT.

Conclusion

AZT-loaded PEC-MUC-PEG microspheres of the desired particle size range of 0.2-0.5 µm and shape were successfully formulated. These microspheres are intended for prolonged intravaginal delivery of AZT.

Part 2 Fabrication of a Pharmaceutical Dosage Form Wherein the PEC-MUC-PEG Microspheres are Formed Together with a Bioerodible Matrix into a Composite Polymeric Caplet.

Aim

To fabricate a pharmaceutical dosage form wherein the PEC-MUC-PEG microspheres are formed together with a bioerodible matrix into a caplet.

Materials and Methods

Materials

Kollidon SR was purchased from Aldrich® (Sigma-Aldrich Inc., St. Louis, USA), Poly D.L lactide was purchased from Boehringer Ingelheim, Ingelheim, Germany. Carbopol 974P NF was obtained from Noveon Inc, Cleveland, Ohio, USA and magnesium stearate was of analytical grade and was utilized as obtained. AZT-loaded PEC-MUC-PEC microspheres were formulated as described previously and simulated vaginal fluid (SVF) was prepared from analytical grade reagents in accordance to Owen and Katz's formulation (*Owen and Katz, 1999*).

Figure 15:
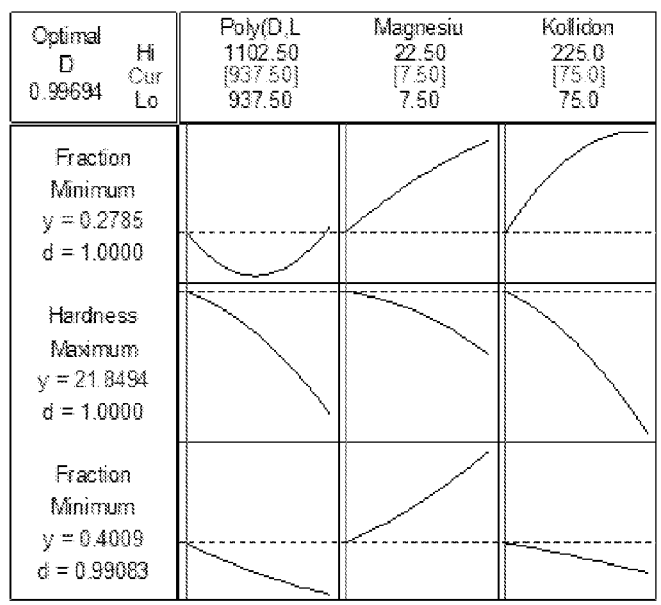
FIG. 15 shows optimized formulation showing desirability, independent variables and computed responses involved in the fabrication of a polymeric caplet.

Measured quantities (according to the Box-Behnken design as presented in Table 6 for the 15 formulations and FIG. 15 for the optimized formulation) of poly DL lactide (PDLL), magnesium stearate (MS), Kollidon SR (KSR), AZT-loaded PEC-MUC-PEG microspheres (20% w/w of total caplet dry weight) and Carbopol 974P NF (1% w/w of total caplet dry weight) were blended for 5 minutes into a uniform dry powder mixture. The powder was then compressed into a caplet using a custom made lab scale punch and die mould on a hydraulic Carver press (Carver Inc, Wabash, Ind., USA) at a compression force of 2.5 tonnes. Different quantities of each ingredient were added in accordance with the formulations generated using a Box-Behnken statistical design. An optimized composite polymeric caplet is thus formed, which is bioerodible in use.

Method:

Fabrication of a Caplet.

Kollidon SR was purchased from Aldrich® (Sigma-Aldrich Inc., St. Louis, USA), Poly D.L lactide was purchased from Boehringer Ingelheim, Ingelheim, Germany. Carbopol 974P NF was obtained from Noveon Inc, Cleveland, Ohio, USA and magnesium stearate was of analytical grade and was utilized as obtained. AZT-loaded PEC-MUC-PEC microspheres were formulated as described previously and simulated vaginal fluid (SVF) was prepared from analytical grade reagents in accordance to Owen and Katz's formulation (*Owen and Katz, 1999*).

Measured quantities (according to the Box-Behnken design as presented in Table 6 for the 15 formulations and FIG. 15 for the optimized formulation) of poly DL lactide (PDLL), magnesium stearate (MS), Kollidon SR (KSR), AZT-loaded PEC-MUC-PEG microspheres (20% w/w of total caplet dry weight) and Carbopol 974P NF (1% w/w of total caplet dry weight) were blended for 5 minutes into a uniform dry powder mixture. The powder was then compressed into a caplet using a custom made lab scale punch and die mould on a hydraulic Carver press (Carver Inc, Wabash, Ind., USA) at a compression force of 2.5 tonnes. Different quantities of each ingredient were added in accordance with the formulations generated using a Box-Behnken statistical design. An optimized composite polymeric caplet is thus formed, which is bioerodible in use.

Box-Behnken Design Optimization of the Caplet

A three-factor, three-level ($3^3$) Box-Behnken statistical design on MINITAB® (V14, State College, Pa., USA) was employed to optimize the fabrication of a composite polymeric caplet. Upper and lower levels of three independent parameters; weight of poly DL lactide (PDLL), weight of magnesium stearate (MS) and the weight of Kollidon SR (KSR) were chosen as a result to their significance in the fabrication the polymeric caplet (Table 5). The responses; fractional weight increase (FWD after 7 days of caplet dissolution in SVF, caplet matrix hardness (H) and fraction of drug released (FDR) after 7 days of caplet dissolution in SVF were sought, as presented in Table 5. Fifteen formulations were generated from the Box-Behnken design as presented in Table 6. These formulations were experimentally tested and the results obtained were fed into the software which then computed the optimized formulation.

TABLE 5

Box-Behnken design variable limits and response objectives

| | Limits (mg) | |
|---|---|---|
| Variable | Lower | Upper |
| weight of poly DL lactide | 1102.5 | 937.5 |
| weight of magnesium stearate | 7.5 | 22.5 |
| weight of Kollidon SR | 75 | |

| Response | Objective |
|---|---|
| fraction of drug release at $t_{7\ days}$ | minimize |
| hardness (N) | maximize |
| fractional SMV* uptake after $t_{7\ days}$ | minimize |

TABLE 6

Box-Behnken design template of 15 formulations

| Formulation | Weight of Poly DL lactide (mg) | Weight of magnesium stearate (mg) | Weight of Kollidon SR (mg) |
|---|---|---|---|
| F1 | 1102.5 | 15 | 225 |
| F2 | 1102.5 | 7.5 | 150 |
| F3 | 1020 | 22.5 | 225 |
| F4 | 937.5 | 15 | 225 |
| F5 | 1020 | 7.5 | 225 |
| F6 | 1102.5 | 22.5 | 75 |
| F7 | 1020 | 22.5 | 75 |
| F8 | 937.5 | 22.5 | 150 |
| F9 | 1020 | 705 | 225 |
| F10 | 937.5 | 7.5 | 150 |
| F11 | 1020 | 15 | 150 |
| F12 | 1102.5 | 15 | 75 |
| F13 | 1020 | 15 | 150 |
| F14 | 937.5 | 15.0 | 75 |
| F15 | 1020 | 7.5 | 75 |

Drug Release Studies of the Caplet

Dissolution studies were performed on the AZT (where the AZT is loaded in the PEC-MUC-PEG microspheres) containing composite polymeric caplet. The caplet was placed in a container and 100 mL of dissolution media was added. The experiment was performed in simulated vaginal fluid (SVF pH4.5). The container was then placed in an orbital shaker incubator (Orbital Shaker Incubator, LM-530D, YIHDER TECHNOLOGY CO., LTD, Jhonghe City, Taipei County, Taiwan, Republic of China) which was kept at 37° C. and rotating at 20 rpm. Aliquots (20410 were withdrawn at predetermined time intervals. The fraction of drug released from the caplet was then computed from the UV absorbance values measured on 4 μL pipette samples of the withdrawn aliquots at 25° C. using a nanophotometer (NanoPhotometer™, Implen GmbH, Munchen, Germany) set to detect UV absorbance at $\lambda_{max}$ of 267 nm. Experiments were performed in triplicate. Dissolution studies were also done in phosphate buffered saline (PBS pH 7.4) which acted as a simulant for semen.

Polymeric Caplet Matrix Hardness Determination

Caplet matrix hardness was tested using a calibrated texture analyzer (Texture Analyzer TA. TX plus, Stable Microsystems, Surrey, UK) fitted with a 5 kg load cell and set at the parameters shown in Table 7. Compression force was measured in triplicate on three different places along the caplet length and a mean value was computed. The peak compression force achieved using a 2 mm flat cylindrical probe was regarded as a measure of the matrix hardness of the caplet. Measurements were done on all the 15 Box-Behnken design template formulations (Table 4).

TABLE 7

Texture Analyzer parameters

| Parameter | Value |
| --- | --- |
| test mode | compression |
| pre-test speed | 1.00 mm/sec |
| test speed | 2.00 mm/sec |
| post-test speed | 10.00 mm/sec |
| target mode | force |
| force | 4N |
| trigger type | auto force |
| trigger force | 0.05N |

Effect of the Quantity of Carbopol 974P NF on Caplet Matrix Dimensional Increase (Swelling)

The effect of the amount (percentage of the total caplet weight) of Carbopol 974P NF of the dimensional increase of the polymeric caplet when exposed to SVF for a month were measured at 1, 2 and 3% Carbopol 974P NF content in the caplet. Caplets were immersed for 30 days in 100 mL SVF filled containers which were then put in an orbital shaker incubator (Orbital Shaker Incubator, LM-530D, YIHDER TECHNOLOGY CO., LTD, Jhonghe City, Taipei County, Taiwan, Republic of China) which was kept at 37° C. and rotating at 20 rpm. The percentage swelling of the caplet was then computed using equation 2:

$$\% \text{ dimensinal increase} \frac{D_2 - D_1}{D_1} \times 100 \quad \text{Equation 2}$$

where:

$D_1$ was the length, width or height of the caplets before being immersed in SVF for 30 days.

$D_2$ was the length, width or height of the caplet after it was immersed in SVF for 30 days.

Results and Discussion

Fabrication and Optimization of the Composite Polymeric Caplet

Figure 13:
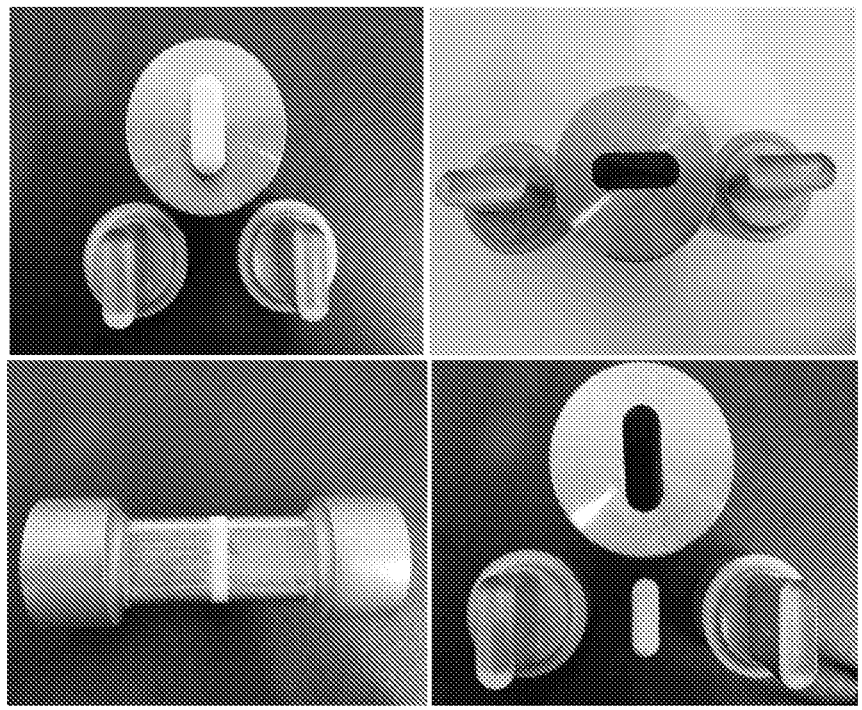
FIG. 13 shows photographic images of a steel punch and die set and polymeric caplets punched using the set.
Figure 14:
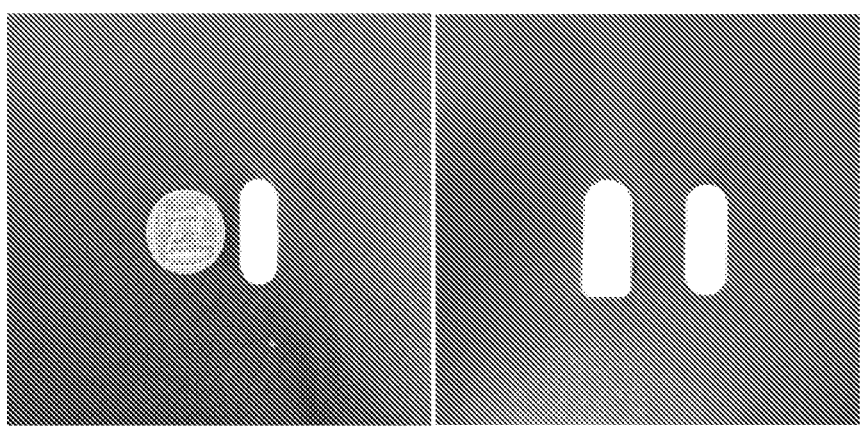
FIG. 14 shows a photographic image of the caplet in comparison to a South African 1 Rand coin and a commercial Bayer Pharmaceuticals' Canesten vaginal tablet.
Figure 16A:
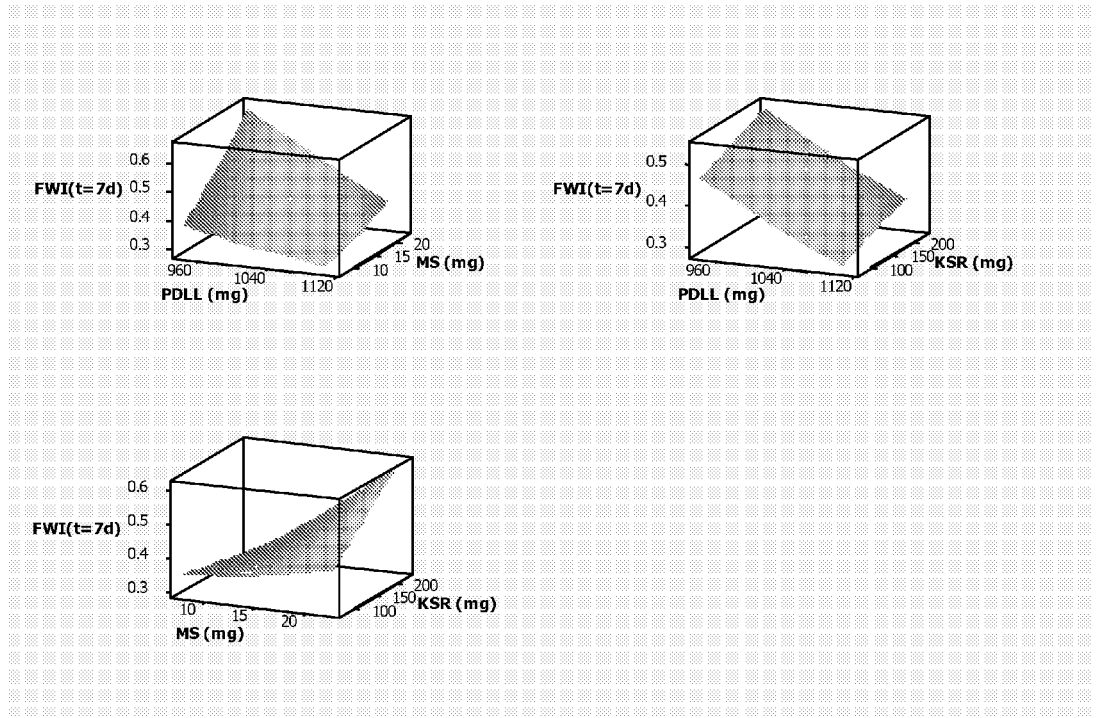
FIG. 16A shows response surface plots correlating fractional of weight increase (FWD to weights of magnesium stearate (MS), Kollidon SR (KSR) and poly-D,L-lactide (PDLL) used in fabricating the polymeric caplet.
Figure 16B:
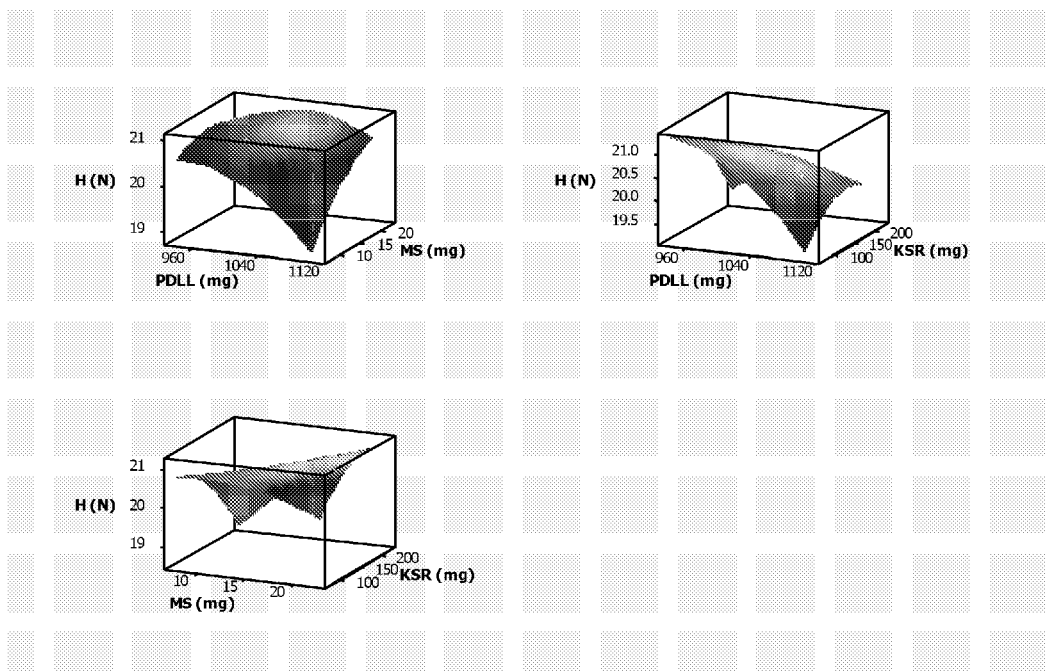
FIG. 16B shows response surface plots correlating matrix hardness (H) to weights of magnesium stearate (MS), Kollidon SR (KSR) and poly-D,L-lactide (PDLL) used in fabricating the polymeric caplet.
Figure 16C:
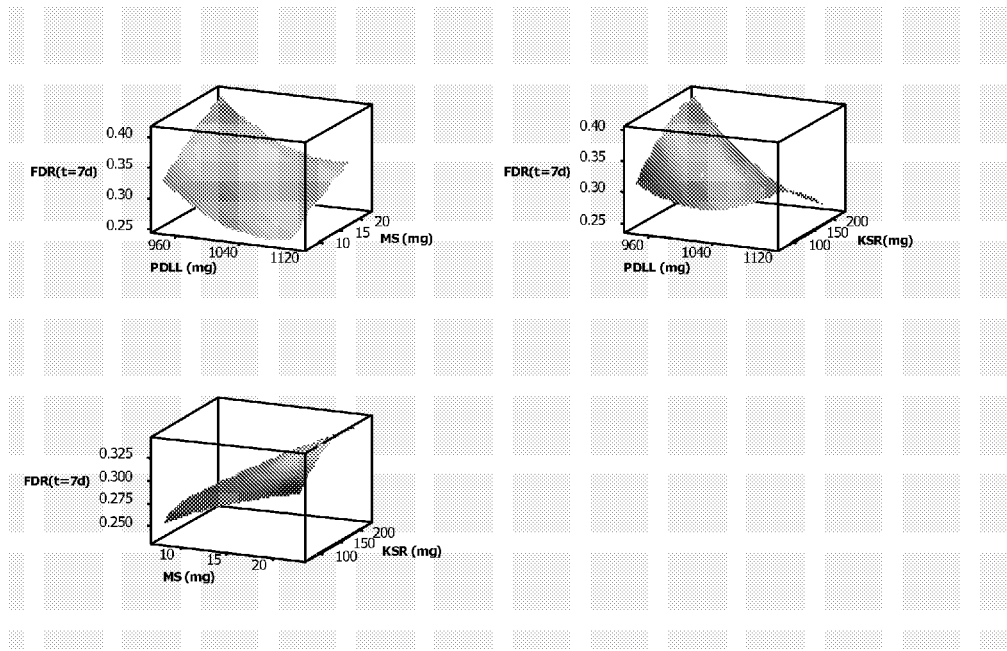
FIG. 16C shows response surface plots correlating fraction of drug released (FDR) to weights of magnesium stearate (MS), Kollidon SR (KSR) and poly-D,L-lactide (PDLL) used in fabricating the polymeric caplet.
Figure 17A:
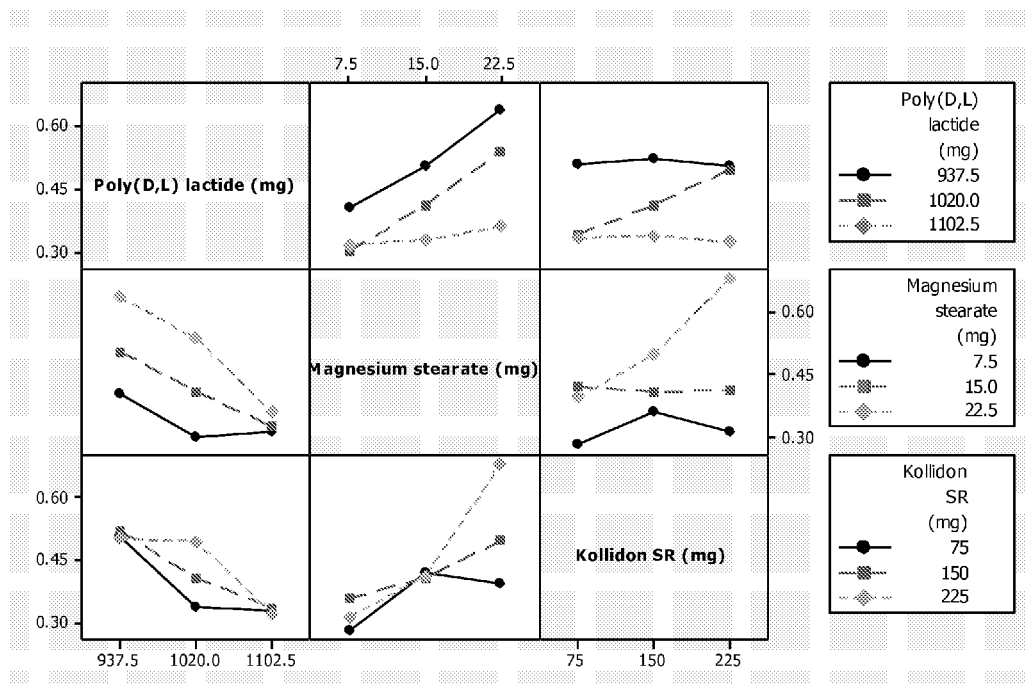
FIG. 17A shows interaction plots of independent variables that occurred to obtain the Fractional weight increase (FWD) response in the optimization of the composite polymeric caplet.
Figure 17B:
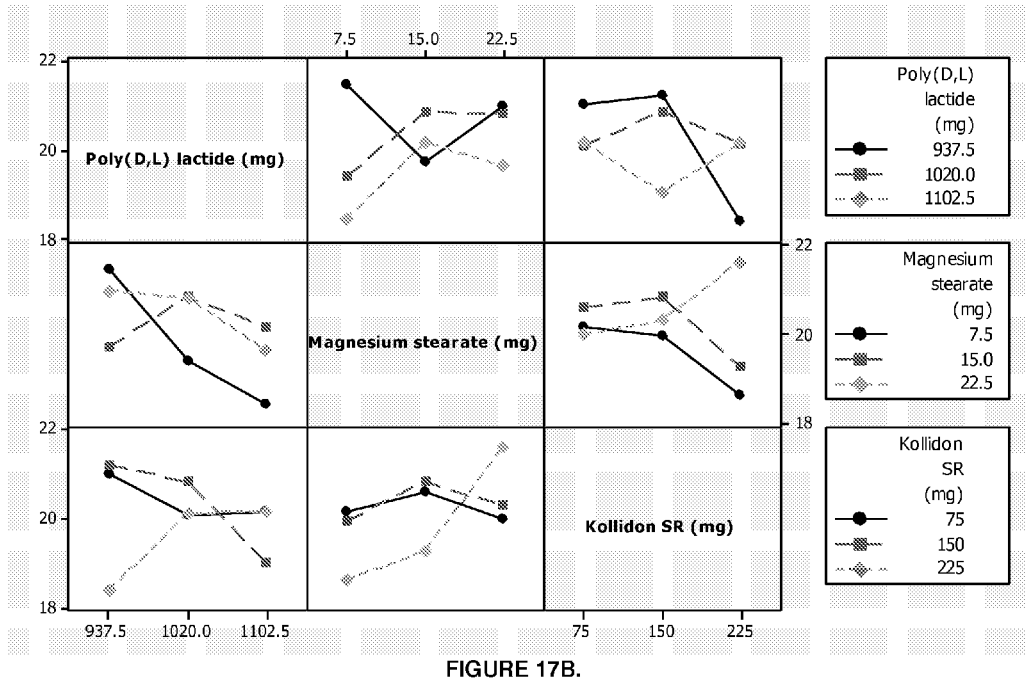
FIG. 17B shows interaction plots of independent variables that occurred to obtain the respective response matrix Hardness (H) in the optimization of the composite polymeric caplet.
Figure 17C:
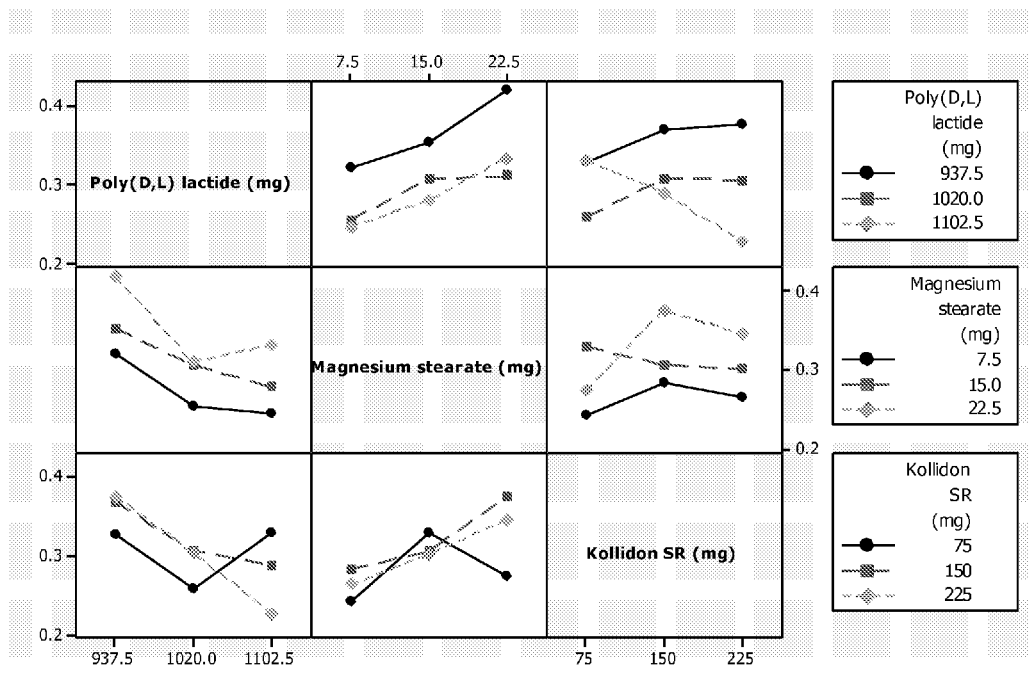
FIG. 17C shows interaction plots of independent variable that occurred to obtain the respective response fraction of drug released (FDR) in the optimization of the composite polymeric caplet.
Figure 18A:
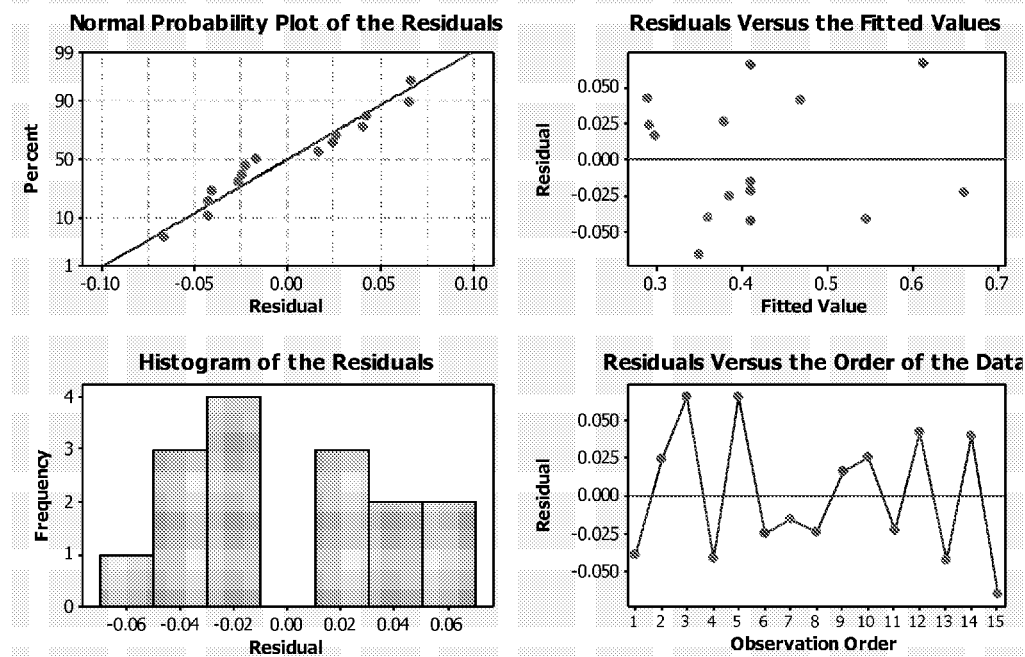
FIG. 18A shows residual Plots of Fractional weight increase in 7 days determined from the Box-Behnken design of the directly compressed caplet.
Figure 18B:
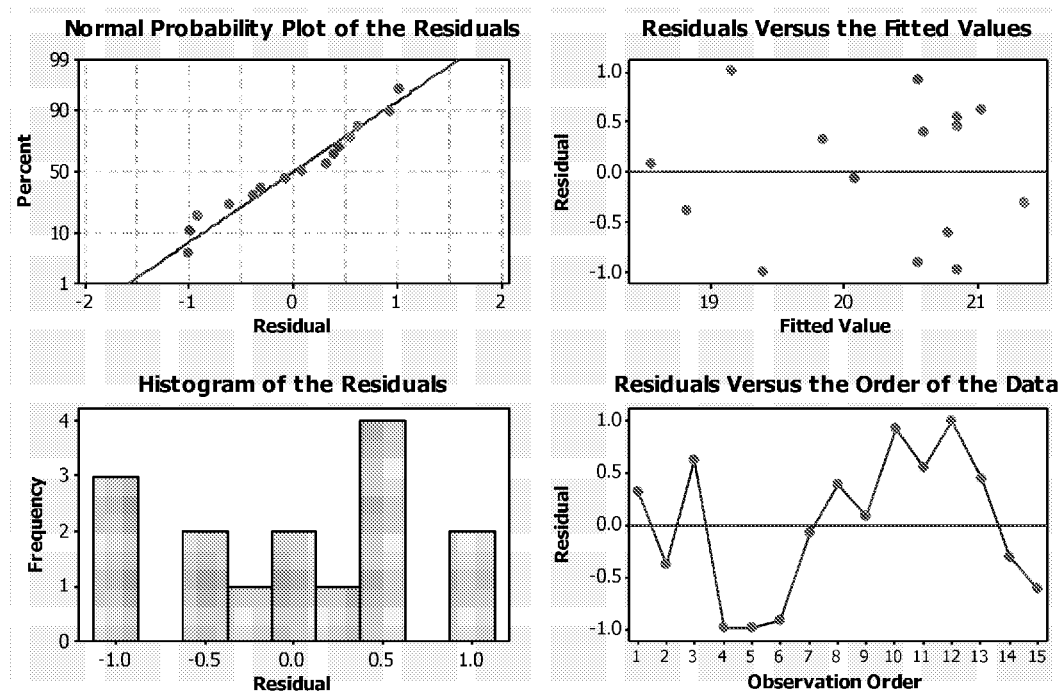
FIG. 18B shows residual Plots of Matrix hardness determined from the Box-Behnken design of the directly compressed caplet.
Figure 18C:
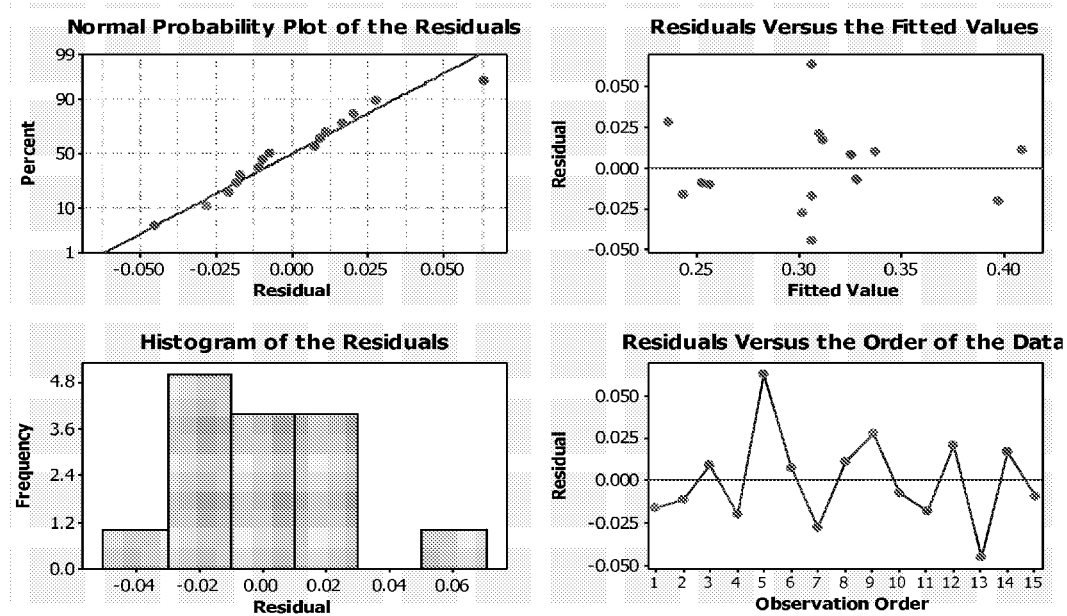
FIG. 18C shows residual Plots Fraction of drug released in 7 days determined from the Box-Behnken design of the directly compressed caplet.

All 15 formulations from the design template were used to fabricate polymeric caplets that took the shape of the custom made punch and die set (FIG. 13). Images of the polymeric caplet in comparison to a South African 1 Rand coin and a commercial product of Canesten vaginal tablet made by Bayer Pharmaceuticals, Germany, are displayed in FIG. 14. The caplets had variable weights and dimensions depending on the amount of materials that was used to fabricate them however the optimized formulation caplet had a length of ~25 mm, width of ~10 mm and height of ~6 mm. Experimental procedure yielded varying results of, fractional weight increase (FWI) after 7 days of caplet dissolution in SVF, caplet matrix hardness (H) and fraction of drug released (FDR) after 7 days of caplet dissolution in SVF (Table 8). These results were then inputted into the Box Behnken software to yield optimized formulation with independent parameters; weight of poly DL lactide (PDLL) as 937.50 mg, weight of magnesium stearate (MS) of 7.5 mg and the weight of Kollidon SR (KSR) of 75 mg (FIG. 15). These independent parameters yielded computed responses, fractional weight increase (FWI) after 7 days of 0.2785, caplet matrix hardness (H) of 21.8494 and fraction of drug released (FDR) of 0.4009 (FIG. 15). The correlation of the responses, fractional weight increase (FWI), caplet matrix hardness (H) and fraction of drug released (FDR) to the independent parameters, weight of poly DL lactide (PDLL), weight of magnesium stearate (MS) and the weight of Kollidon SR (KSR) are illustrated as response surface plots presented in FIGS. 16a-c. How the independent parameters contribute towards the responses observed in the fabrication of the caplet is illustrated by the interaction plots in FIGS. 17a-c and how the formulation responses are distributed in respect of the independent variables are depicted in the different residual plots in FIGS. 18a-c.

TABLE 8

Experimental responses to the 15 design formulations used in the optimization for the polymeric caplet

| Formulation | Fractional weight increase after 7 days in SMV* | Hardness (N) | Fraction of drug released in SVF after 7 days |
| --- | --- | --- | --- |
| F1 | 0.320 | 20.152 | 0.227 |
| F2 | 0.314 | 18.438 | 0.245 |
| F3 | 0.678 | 21.634 | 0.346 |
| F4 | 0.502 | 18.400 | 0.376 |
| F5 | 0.474 | 19.849 | 0.369 |
| F6 | 0.358 | 19.634 | 0.332 |
| F7 | 0.394 | 19.997 | 0.274 |
| F8 | 0.635 | 20.977 | 0.419 |
| F9 | 0.314 | 18.636 | 0.264 |
| F10 | 0.404 | 21.473 | 0.320 |
| F11 | 0.386 | 21.384 | 0.288 |
| F12 | 0.330 | 20.158 | 0.330 |
| F13 | 0.366 | 21.286 | 0.261 |
| F14 | 0.507 | 21.031 | 0.328 |
| F15 | 0.284 | 20.164 | 0.243 |

*simulated vaginal fluid

Drug Release from Polymeric Caplet

Figure 19A:
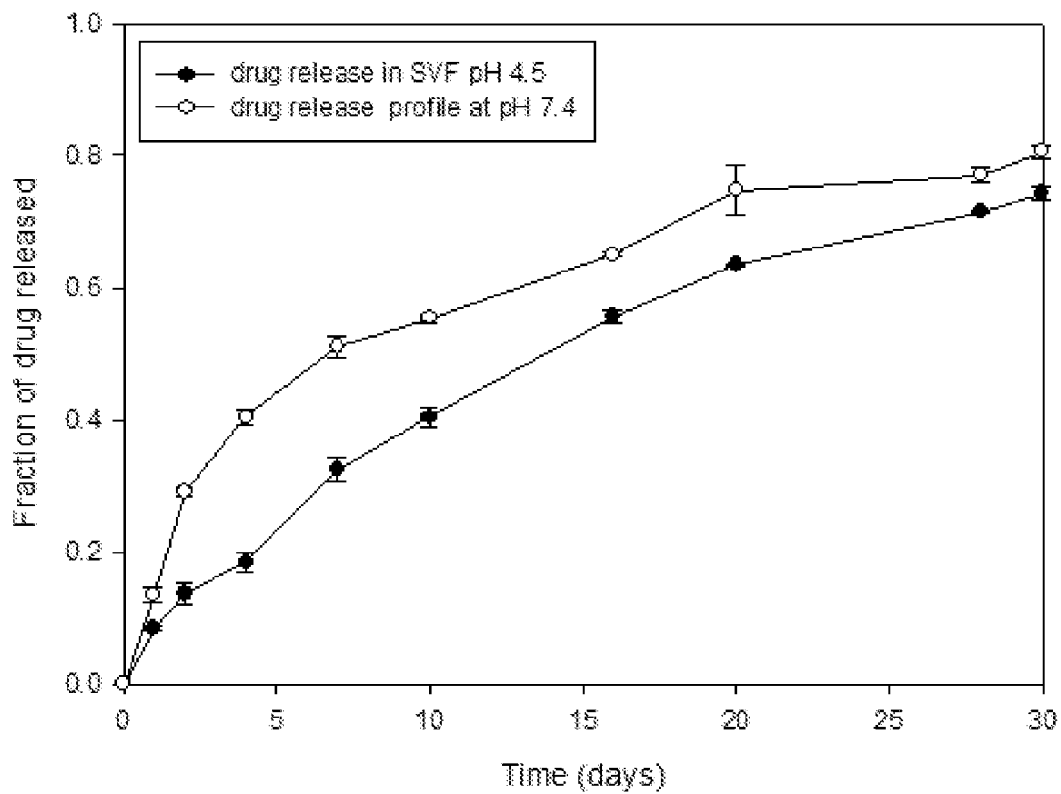
FIG. 19A shows the fraction of AZT released from the optimised formulation of the polymeric caplet in SVF and PBS.
Figure 19B:
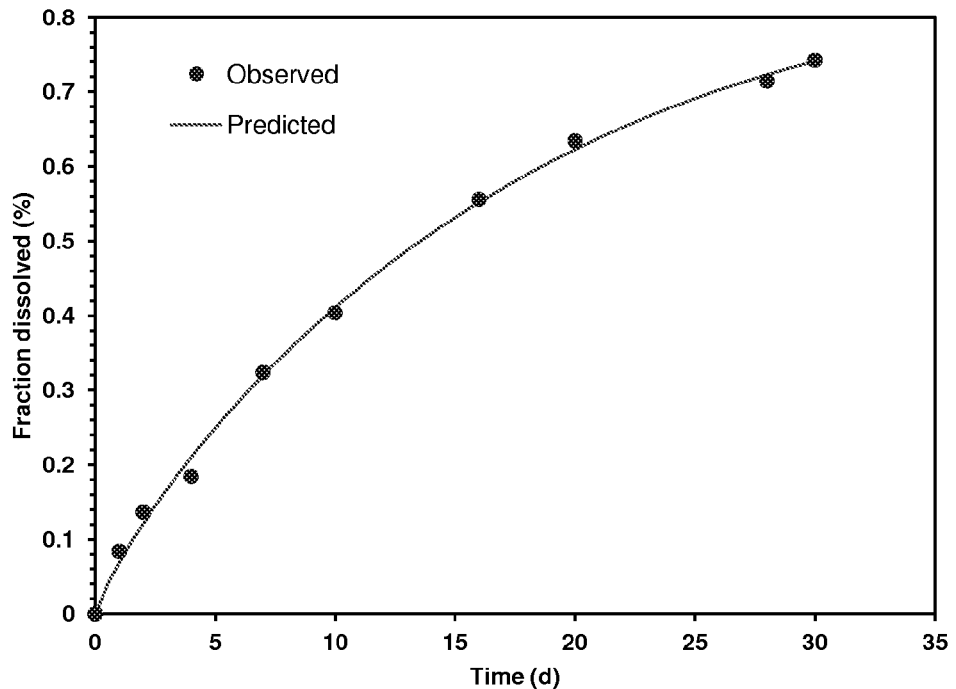
FIG. 19B shows the AZT release profile from the caplet in SVF pH 4.5 fitted on the Makoid-Banakar model.
Figure 19C:
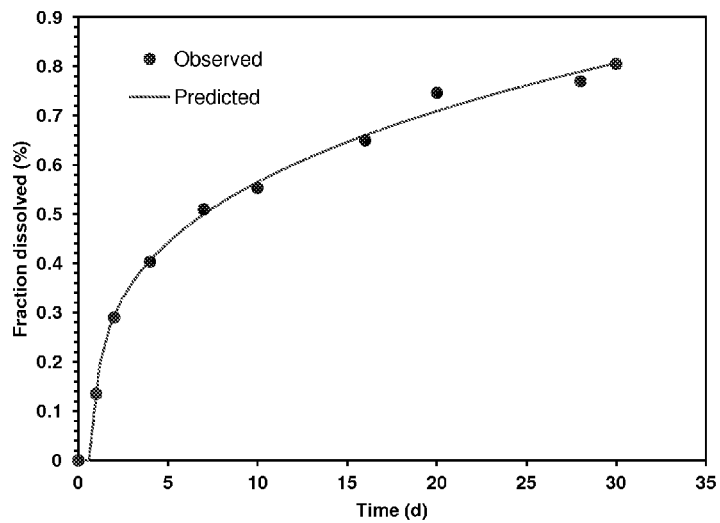
FIG. 19C shows the AZT release profile from the caplet in phosphate buffered saline (PBS) pH 7.4 fitted to the Webull model.

The fraction of AZT released from the polymeric caplet was measured for 7 days for the 15 design formulations as shown in Table 8. The fraction of drug released varied from 0.227 in Formulation F1 to 0.419 in Formulation F8 (Table 8). The optimized formulation had a computed fraction of drug released within 7 days of 0.4009. The fraction of drug release of optimised formulation was then experimentally tested in both SVF and PBS (acted as a semen simulant) for duration of 30 days and these results of experiments are depicted in FIGS. 19a-c. The fraction of drug released in SVF pH 4.5 was 0.7425±0.0104 and that release in PBS pH 7.4 was 0.8056±0.0100. This showed an increase in the fraction of drug released at pH 4.5 and that released at pH 7.4 and this could be a result of the contribution by the 1% Carbopol composition of the polymeric caplet. Carbopol is pH responsive because of the several carboxylic groups it possesses which are ionized in basic media (PBS pH 7.4) and are not ionized in acidic media (SVF pH 4.5). The ionized carboxylic groups in PBS might have repelled each other causing increase in water uptake by the caplet, swelling and destabilization of the caplet matrix which then resulted in an increase in drug release (FIG. 19). In addition the increase in the fraction of drug released when pH increased from 4.5 to 7.4 may have been contributed by pectin (PEC) and porcine gastric mucin (MUC) that form part of the microsphere architecture. At increased pH the hydroxyl groups found on pectin and mucin ionize and repel each other leading to the destabilization of the microsphere architecture which intern results in an increased release rate of the pharmaceutical compound from the microsphere and wherein a decrease in pH facilitates a decrease in the release rate of the pharmaceutical compound from the microsphere.

Polymeric Caplet Hardness

Figure 20:
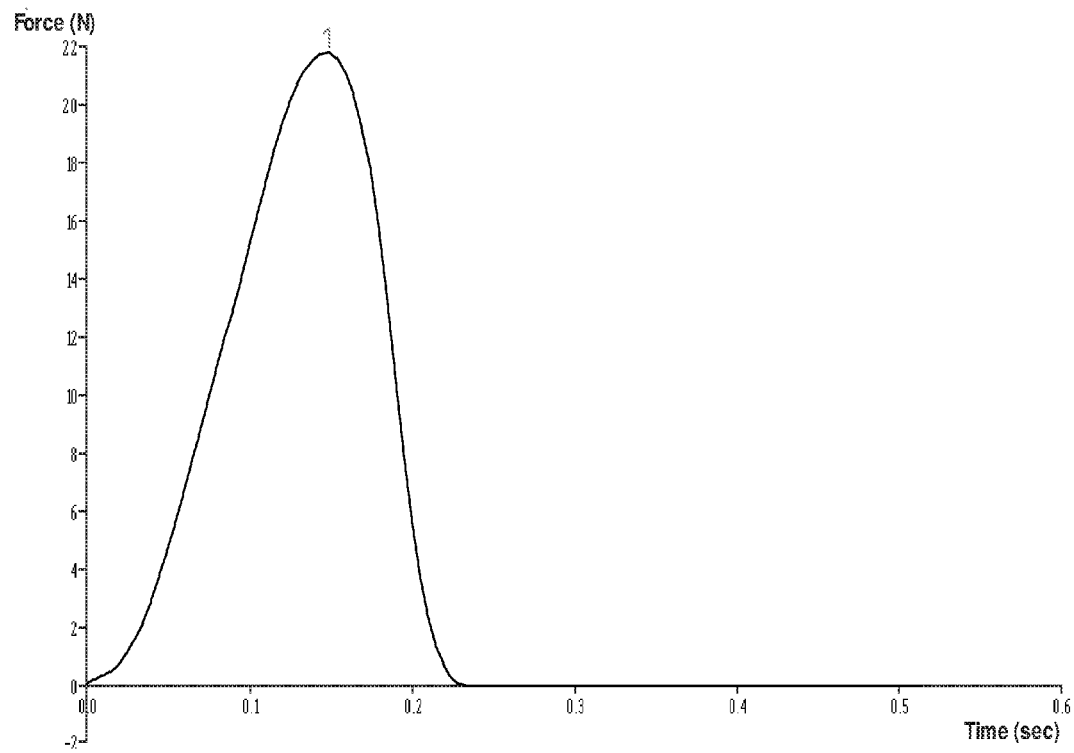
FIG. 20 shows composite polymeric caplet hardness.

Caplet matrix hardness values of the 15 design formulations were measured and are presented in Table 8. These varied from 18.400N in Formulation F11 to 21.634N in Formulation F15 (Table 8). The optimized formulation had a computed caplet matrix hardness of 21.849 whilst the measured hardness was 22.061±0.261N (FIG. 20).

Effect of the Quantity of Carbopol 974P NF on Caplet Matrix Swelling

Figure 21:
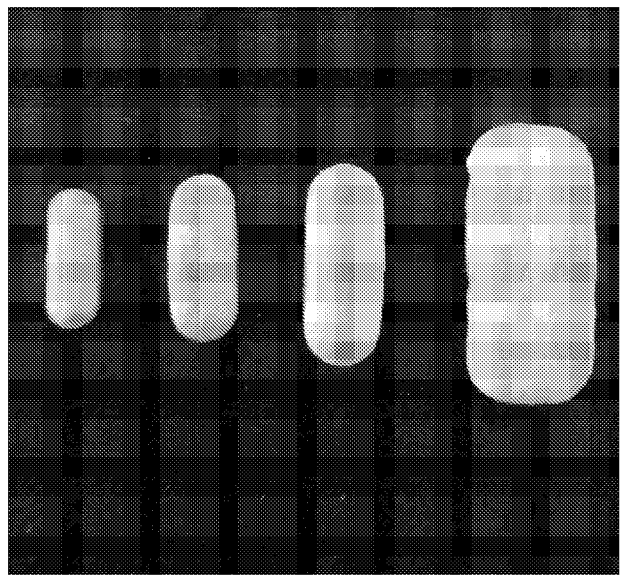
FIG. 21 shows images of the polymeric caplet, from left to right; containing 1%, 2% or 3% Carbopol 974P NF before exposure to SVF, containing 1% Carbopol 974P NF after 1 month exposure to SVF, containing 2% Carbopol 974P NF after 1 month exposure to SVF and containing 3% Carbopol 974P NF after 1 month exposure to SVF.
Figure 22:
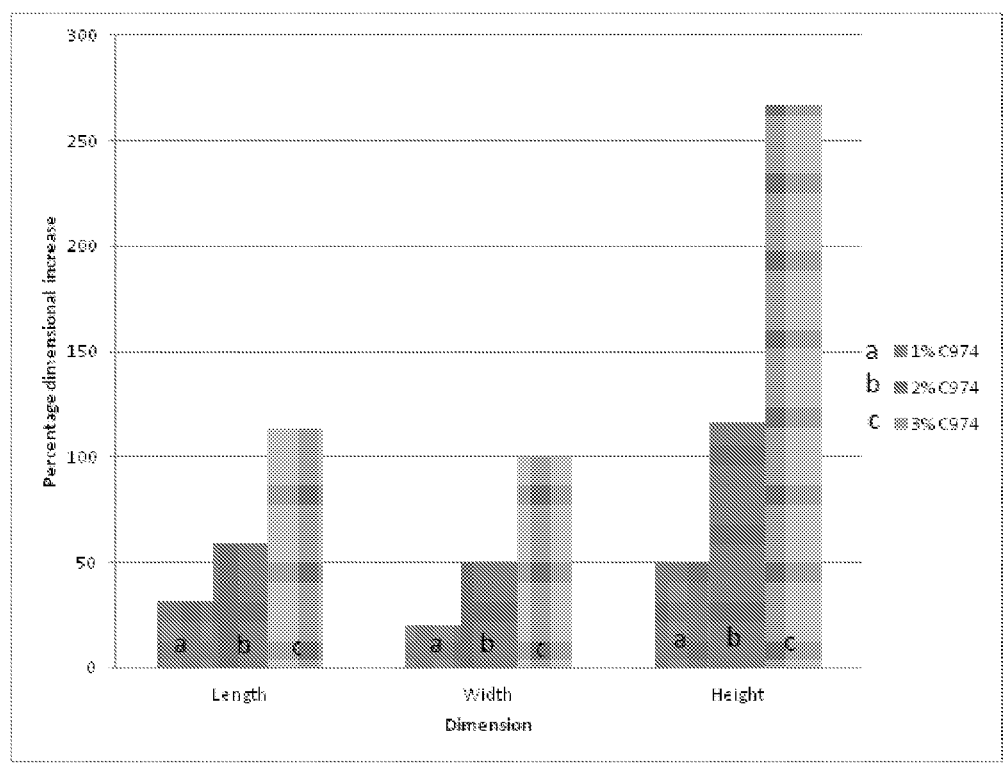
FIG. 22. shows the effect of carbopol 974p of (c974) on dimensions of the caplet after 30 days dissolution in simulated vaginal fluid.

The amount (percentage of the total caplet weight) of Carbopol 974P NF in the caplet determined the degree of SVF uptake and hence its % dimensional increase (swelling). Images of the polymeric caplet containing 1%, 2% or 3% Carbopol 974P NF before exposure to SVF, containing 1% Carbopol 974P NF after 1 month exposure to SVF, containing 2% Carbopol 974P NF after 1 month exposure to SVF and that containing 3% Carbopol 974P NF after 1 month exposure to SVF are depicted in FIG. 21. The percentage dimensional increase in length, with and height of the caplet are depicted in FIG. 22.

REFERENCES

Van Damme, L., Ramjee, G., Alary, M., Vuylsteke, B., Chandeying, V., Rees, H., Sirivongrangson, P., Mukenge-Tshibaka, L., Ettiègne-Traoré, V., Uaheowitchai, C., Karim, S. S., Mâsse, B., Perriër's, J., Laga, M., COL-1492 Study Group., Effectiveness of COL-1492, a nonoxynol-9 vaginal gel, on HIV-1 transmission in female sex workers: a randomised controlled trial. Lancet 360 (2002), pp. 971-977.

Kumar, M., Mishra, R. K., Banthia A. K., Development of pectin based hydrogel membranes for biomedical applications. International Journal of Plastic Technology 14 (2010), pp. 213-223.

Owen, D. H., Katz, D. F., A vaginal fluid simulant. Contraception 59 (1999), pp. 91-95.

CONCLUSION

A composite polymeric dosage form in the form of a caplet comprising of AZT-loaded PEC-MUC-PEC microspheres embedded within a polymeric matrix was successfully fabricated. Further test need to be done to characterize the caplet matrix such as porosity of the caplet before and after in vitro dissolution, erosion studies, friability tests and most importantly in vivo tests in an animal model such as the Large White pig. These animal studies will examine in vivo stability, drug release and compatibility of the polymeric dosage form.

It is to be understood that the pharmaceutical dosage form as defined in this disclosure may be for use in treating a sexually transmitted infection/disease and/or for use in prophylaxis against a sexually transmitted infection/disease comprising intravaginal administration of the pharmaceutical dosage form to a person in need thereof.

There is also provided for a method of treating a sexually transmitted infection/disease and/or a method of prophylaxis against a sexually transmitted infection/disease comprising intravaginal administration of the pharmaceutical dosage form as defined in this disclosure.

While the invention has been described in detail with respect to specific embodiments and/or examples thereof, it will be appreciated that those skilled in the art, upon attaining an understand of the foregoing may readily conceive of alterations to, variations of and equivalents to these embodiments. Accordingly, the scope of the present invention should be assessed as that of the appended claims and any equivalents thereto.

The invention claimed is:

1. A method of treating a sexually transmitted infection/disease and/or a method of prophylaxis against a sexually transmitted infection/disease comprising intravaginal administration of a pharmaceutical dosage form comprising a pharmaceutical compound and a microsphere comprising a pectin (PEC) framework providing rigidity to the microsphere, porcine gastric mucin (MUC) substantially encapsulated and/or embedded in the pectin (PEC) framework, and polyethylene glycol (PEG), to a person in need thereof, wherein, in use, the PEG provides a neutral charge facilitating passage of the microspheres across vaginal mucus lining the target site, the target site located on the vaginal wall, and wherein the PEC and MUC modulate release of the pharmaceutical compound at the target site in a pH-dependent manner, wherein an increase in pH facilitates an increase in the release rate of the pharmaceutical compound from the microsphere and wherein a decrease in pH facilitates a decrease in the release rate of the pharmaceutical compound from the microsphere.

2. The method of claim 1, wherein the PEG is in the form of a hydrophilic coating around the microsphere to form a PEC-MUC-PEG microsphere.

3. The method of claim 1, wherein the PEG is blended with the microsphere to form a monolithic PEC-MUC-PEG microsphere.

4. The method of claim 1, wherein the PEG is a low molecular weight PEG having a molecular weight of about 400 g/mol, and the MUC is porcine gastric mucin type III (MUC III).

5. The method of claim 1, wherein the pharmaceutical dosage form comprises a plurality of microspheres.

6. The method of claim 5, wherein the microspheres each have a diameter in the range of about 0.2 to about 0.5 micrometers to facilitate, when used intravaginally, the passage of the microspheres across vaginal mucus lining the target site, the target site located on the vaginal wall.

7. The method of claim 5, wherein the pharmaceutical dosage form further comprises a bioerodible polymeric matrix which is associated with the microspheres, wherein when the pharmaceutical dosage form is inserted into the vagina, the bioerodible polymeric matrix erodes over a predetermined time period therein releasing the microspheres which, in turn, release the pharmaceutical compound intravaginally.

8. The method of claim 7, wherein the bioerodible polymeric matrix comprises at least one of hydrophilic polymers, hydrophobic polymers, poly(acrylic acids)

(PAA), poly(lactic acids) (PLA), carageenans, polystyrene sulfonate, polyamides, polyethylene oxides, cellulose, poly(vinylpyrrolidone) (PVP), poly(vinyl alcohol) (PVA), chitosan, poly(ethyacrylate), methylmethacrylate, chlorotrimethyl ammonium methylmethacrylate, hydroxyapatite, pectin, porcine gastric mucin, poly(sebacic acid) (PSA), hydroxypropyl methylcellulose (HPMC), cellulose acetate phthalate (CAP), magnesium stearate (MS), polyethylene glycol, gum-based polymers and variants thereof, poly(D,L)-lactide (PDLL), polyvinyl acetate and povidone, carboxypolymethylene, and derivatives thereof.

9. The method of claim 7, wherein the pharmaceutical dosage form is formed into a caplet or a tablet, which caplet or tablet comprises the bioerodible polymeric matrix which substantially encapsulates and/or embeds the microsphere, such that in use, bioerosion of the matrix results in release of the microsphere which, in turn, releases the pharmaceutical compound.

10. The method of claim 1, wherein the pharmaceutical compound is an antiretroviral and/or a microbicide.

11. The method of claim 10, wherein the antiretroviral comprises at least one of: zidovudine, lamivudine, abacavir, lopinavir, ritonavir, emtricitabine, efavirenz, tenofovir, pharmaceutically acceptable salts of the antiretroviral, and compositions containing the antiretroviral.

12. The method of claim 10, wherein the microbicide comprises at least one of: kappa carageenan, carbomer, cellulose acetate phthalate, capric acid, polystyrene sulfonate, carageenan, monocaprin, polyacrylic acid, lactobacillus, cellulose sulfate, naphthalene sulfonate, sulfated polyvinyl alcohol, lactic acid, cetyl betaine, myristamine oxide, stampidine, cyanovirin-n, monoclonal antibodies, lyposomes, thrombospondin-1, lime juice, yoghurt, tenofovir, zidovudine, dendrimers, thiourea, silver, polystyrene, sodium lauryl sulphate, pharmaceutically acceptably salts of the microbicide, and compositions containing the microbicide.

13. The method of claim 1, wherein the pharmaceutical dosage form comprises a pharmaceutical compound and a plurality of microspheres each consisting of PEC, MUC and PEG, wherein the multitude of microspheres are blended together with a bioerodible polymeric matrix consisting of poly(D,L)-lactide (PDLL), magnesium stearate (MS), polyvinyl acetate and povidone, carboxypolymethylene in caplet form, wherein the caplet is inserted into the vagina and the bioerodible polymeric matrix erodes over a predetermined time period therein releasing the multitude of microspheres which each, in turn, release the pharmaceutical compound intravaginally.

14. The method of claim 8, wherein the pharmaceutical dosage form is formed into a caplet or a tablet, which caplet or tablet comprises the bioerodible polymeric matrix which substantially encapsulates and/or embeds the microsphere, such that in use, bioerosion of the matrix results in release of the microsphere which, in turn, releases the pharmaceutical compound.

* * * * *